US011510946B2

(12) United States Patent
Marom et al.

(10) Patent No.: US 11,510,946 B2
(45) Date of Patent: Nov. 29, 2022

(54) TREATMENT OF MULTIPLE SCLEROSIS WITH ADIPOSE-DERIVED STEM CELLS

(71) Applicant: STEM CELL MEDICINE LTD., Jerusalem (IL)

(72) Inventors: Ehud Marom, Tel Aviv (IL); Frida Grynspan, Mevaseret Zion (IL); Dima Yudin, Jerusalem (IL)

(73) Assignee: STEM CELL MEDICINE LTD., Jerusalem (IL)

( * ) Notice: Subject to any disclaimer, the term of this patent is extended or adjusted under 35 U.S.C. 154(b) by 94 days.

(21) Appl. No.: 16/613,369

(22) PCT Filed: May 14, 2018

(86) PCT No.: PCT/IL2018/050523
§ 371 (c)(1),
(2) Date: Nov. 13, 2019

(87) PCT Pub. No.: WO2018/211498
PCT Pub. Date: Nov. 22, 2018

(65) Prior Publication Data
US 2020/0188439 A1 Jun. 18, 2020

Related U.S. Application Data

(60) Provisional application No. 62/506,006, filed on May 15, 2017.

(51) Int. Cl.
| | | |
|---|---|---|
| *A61K 35/28* | (2015.01) | |
| *A61K 9/00* | (2006.01) | |
| *C12N 5/0775* | (2010.01) | |
| *A61P 21/00* | (2006.01) | |

(52) U.S. Cl.
CPC ............ *A61K 35/28* (2013.01); *A61K 9/0019* (2013.01); *A61K 9/0085* (2013.01); *A61P 21/00* (2018.01); *C12N 5/0667* (2013.01); *C12N 2523/00* (2013.01)

(58) Field of Classification Search
None
See application file for complete search history.

(56) References Cited

U.S. PATENT DOCUMENTS

| | | |
|---|---|---|
| 3,849,550 A | 11/1974 | Teitelbaum et al. |
| 5,981,589 A | 11/1999 | Konfino et al. |
| 6,048,898 A | 4/2000 | Konfino et al. |
| 6,054,430 A | 4/2000 | Konfino et al. |
| 6,214,791 B1 | 4/2001 | Arnon et al. |
| 6,342,476 B1 | 1/2002 | Konfino et al. |
| 6,362,161 B1 | 3/2002 | Konfino et al. |
| 6,620,847 B2 | 9/2003 | Konfino et al. |
| 6,844,314 B2 | 1/2005 | Eisenbach-Schwartz et al. |
| 6,939,539 B2 | 9/2005 | Konfino et al. |
| 8,008,258 B2 | 8/2011 | Aharoni et al. |
| 8,021,882 B2 | 9/2011 | Johnstone et al. |
| 8,216,566 B2 | 7/2012 | Paludan et al. |
| 8,377,885 B2 | 2/2013 | Marom et al. |
| 8,404,866 B2 | 3/2013 | Schwartz et al. |
| 8,642,331 B2 | 2/2014 | Sadiq et al. |
| 8,679,834 B2 | 3/2014 | Lombardo et al. |
| 8,703,180 B1 | 4/2014 | Stankus et al. |
| 8,785,199 B2 | 7/2014 | Hotta |
| 8,796,226 B2 | 8/2014 | Marom et al. |
| 9,200,114 B2 | 12/2015 | Marom et al. |
| 2007/0269413 A1 | 11/2007 | Serhan et al. |
| 2008/0063687 A1 | 3/2008 | Chou et al. |
| 2009/0148149 A1 | 6/2009 | Gonzalez et al. |
| 2009/0148419 A1 | 6/2009 | Gonzalez De La Pena et al. |
| 2009/0191173 A1 | 7/2009 | Eisenbach-Schwartz |
| 2009/0291061 A1 | 11/2009 | Riordan et al. |
| 2011/0008300 A1* | 1/2011 | Wouters ............... A61P 35/00 424/93.7 |
| 2011/0129450 A1 | 6/2011 | Lazarov et al. |
| 2012/0015891 A1 | 1/2012 | Marom et al. |
| 2012/0064098 A1 | 3/2012 | Consigny et al. |
| 2012/0164229 A1 | 6/2012 | Marom |
| 2012/0230966 A1 | 9/2012 | Crawford et al. |
| 2013/0034524 A1 | 2/2013 | Agha-Mohammadi |
| 2013/0156725 A1 | 6/2013 | Marom |
| 2014/0037598 A1 | 2/2014 | Jansen et al. |
| 2014/0140968 A1 | 5/2014 | Kadouri et al. |

(Continued)

FOREIGN PATENT DOCUMENTS

| | | |
|---|---|---|
| EP | 1592384 B1 | 10/2012 |
| EP | 1827108 B1 | 4/2015 |

(Continued)

OTHER PUBLICATIONS

Shalaby SM, Sabbah NA, Saber T, Abdel Hamid RA. Adipose-derived mesenchymal stem cells modulate the immune response in chronic experimental autoimmune encephalomyelitis model. IUBMB Life. Feb. 2016;68(2):106-15. (Year: 2016).*
Mirabet V, Alvarez M, Solves P, Ocete D, Gimeno C. Use of liquid nitrogen during storage in a cell and tissue bank: contamination risk and effect on the detectability of potential viral contaminants. Cryobiology. Apr. 2012;64(2):121-3. (Year: 2012).*
Abeam. (Jan. 10, 2016). Cryopreservation of mammalian cell lines video protocol, https://www.abcam.com/protocols/cryopreservation-of-mammalian-cell-lines-video-protocol (Year: 2016).*
Bai X, Yan Y, Song YH, Seidensticker M, Rabinovich B, Metzele R, Bankson JA, Vykoukal D, Alt E. Both cultured and freshly isolated adipose tissue-derived stem cells enhance cardiac function after acute myocardial infarction. Eur Heart J. Feb. 2010;31(4):489-501. (Year: 2010).*

(Continued)

*Primary Examiner* — Emily A Cordas
(74) *Attorney, Agent, or Firm* — Rothwell, Figg, Ernst & Manbeck, P.C.

(57) ABSTRACT

Methods of treating progressive forms of multiple sclerosis are provided, comprising administering adipose-derived stem cells into the central nervous system (CNS). Further provided are improved methods for obtaining ADSCs, which are more cost effective and which provide higher yields compared to currently used methods.

10 Claims, 9 Drawing Sheets

(56) References Cited

U.S. PATENT DOCUMENTS

| | | |
|---|---|---|
| 2014/0234272 A1 | 8/2014 | Vesey et al. |
| 2014/0308745 A1 | 10/2014 | Sadiq et al. |
| 2014/0315870 A1 | 10/2014 | Conget Molina et al. |
| 2015/0030662 A1 | 1/2015 | Raghunath et al. |
| 2015/0216908 A1 | 8/2015 | Lee et al. |
| 2017/0065638 A1* | 3/2017 | Fraser .................... A61P 25/00 |

FOREIGN PATENT DOCUMENTS

| | | |
|---|---|---|
| JP | 2008521796 A | 6/2008 |
| JP | 2013516403 A | 5/2013 |
| JP | 2015511221 A | 4/2015 |
| JP | 2020519645 A | 7/2020 |
| WO | 2006057003 A2 | 6/2006 |
| WO | 2006060779 A2 | 6/2006 |
| WO | 2010045645 A1 | 4/2010 |
| WO | 2011080733 A1 | 7/2011 |
| WO | 2017139795 A1 | 8/2017 |
| WO | 2018002930 A1 | 1/2018 |

OTHER PUBLICATIONS

Zhu M, Heydarkhan-Hagvall S, Hedrick M, Benhaim P, Zuk P. Manual isolation of adipose-derived stem cells from human lipoaspirates. J Vis Exp. Sep. 26, 2013;(79):e50585. (Year: 2013).*

Ra et al. "Stem cell treatment for patients with autoimmune disease by systemic infusion of culture-expanded autologous adipose tissue derived mesenchymal stem cells." Journal of translational medicine 9.1 (2011): 1-11. (Year: 2011).*

Choudhery et al., (2014) Cryopreservation of whole adipose tissue for future use in regenerative medicine. J Surg Res 187(1): 24-35.

Giacoppo et al., (2017) The transplantation of mesenchymal stem cells derived from unconventional sources: an innovative approach to multiple sclerosis therapy. Arch Immunol Ther Exp (Warsz) 65(5): 363-379.

Gong et al., (2012) Banking human umbilical cord-derived mesenchymal stromal cells for clinical use. Cell Transplant 21(1): 207-216.

Aharoni et al., (2009) Transplanted myogenic progenitor cells express neuronal markers in the CNS and ameliorate disease in experimental autoimmune encephalomyelitis, J Neuroimmunol, 215(1-2): 73-83.

Baer and Geiger (2012) Adipose-derived mesenchymal stromal/stem cells: tissue localization, characterization, and heterogeneity. Stem Cells Int, 2012: 812693; 12 pages.

Barhum et al., (2009) Intracerebroventricular transplantation of human mesenchymal stem cells induced to secrete neurotrophic factors attenuates clinical symptoms in a mouse model of multiple sclerosis, J Mol Neurosci, 41(1): 129-137.

Bunnell et al., (2008) Adipose-derived stem cells: isolation, expansion and differentiation, Methods, 45(2): 115-120.

Constantin et al., (2009) Adipose-derived mesenchymal stem cells ameliorate chronic experimental autoimmune encephalomyelitis. Stem Cells, 27(10): 2624-2635.

Devitt et al., (2015) Successful isolation of viable adipose-derived stem cells from human adipose tissue subject to long-term cryopreservation: positive implications for adult stem cell-based therapeutics in patients of advanced age, Stem Cells Int, 2015: 146421; 12 pages.

Doshi and Chataway (2016) Multiple sclerosis, a treatable disease, Clin Med (Lond), 16(Suppl 6): s53-s59.

Hayon et al., (2012) Platelet microparticles promote neural stem cell proliferation, survival and differentiation, J Mol Neurosci, 47(3): 659-665.

Menard et al., (2013) Clinical-grade mesenchymal stromal cells produced under various good manufacturing practice processes differ in their immunomodulatory properties: standardization of immune quality controls, Stem Cells Dev, 22 (12): 1789-1801.

Muraro et al., (2017) Long Term Outcomes after Autologous Hematopoietic Stem Cell Transplantation for Multiple Sclerosis. JAMA Neurol. Author manuscript; available in PMC Dec. 27, 2017. 19 pages.

Pisati et al., (2007) Induction of neurotrophin expression via human adult mesenchymal stem cells: implication for cell therapy in neurodegenerative diseases, Cell Transplant, 16(1): 41-55.

Shinmura et al., (2011) Pretreatment of human mesenchymal stem cells with pioglitazone improved efficiency of cardiomyogenic transdifferentiation and cardiac function, Stem Cells, 29(2): 357-366.

Sorensen et al., (1998) Intravenous immunoglobulin G reduces MRI activity in relapsing multiple sclerosis, Neurology, 50(5): 1273-1281.

Stepien et al., (2016) Clinical Application of Autologous Adipose Stem Cells in Patients with Multiple Sclerosis: Preliminary Results, Mediators Inflamm, 2016: 5302120; 6 pages.

Tsuji et al., (2014) Adipose-derived stem cells: Implications in tissue regeneration, World J Stem Cells, 6(3): 312-321.

Wilkins et al., (2009) Human bone marrow-derived mesenchymal stem cells secrete brain-derived neurotrophic factor which promotes neuronal survival in vitro, Stem Cell Res, 3(1): 63-70.

Zuk et al., (2002) Human adipose tissue is a source of multipotent stem cells, Mol Biol Cell, 13(12): 4279-4295.

Azevedo Margarida; "Promising Phase 1 Trial Results of Stem Cell Therapy in Progressive MS Patients Being Presented at AAN Meeting", Multiple Sclerosis News Today Apr. 19, 2016, Retrieved from: https://multiplesclerosisnewstoday.com/news-posts/2016/04/19/promising-phase-1-trial-results-stem-cell-therapy-progressive-ms-patients-presented-aan-meeting/ on Oct. 22, 2019; 6 pages.

Silva Patricia; "Research on Faulty Stem Cells Suggests MS Patients Need Tailored Therapies", Multiple Sclerosis News Today, Apr. 4, 2017, Retrieved from: https://multiplesclerosisnewstoday.com/2017/04/04/study-on-faulty-multiple-sclerosis-stem-cells-suggests-patients-need-tailored-therapies/on Oct. 22, 2019; 7 pages.

U.S. FDA grants Breakthrough Therapy Designation for Roche's investigational medicine ocrelizumab in primary progressive multiple sclerosis, Investor Update. Basel, Feb. 17, 2016, Retrieved from: https://www.roche.com/investors/updates/inv-update-2016-02-17.htm on Oct. 10, 2019; 5 pages.

Bonab et al., (2012) Autologous mesenchymal stem cell therapy in progressive multiple sclerosis: an open label study, Curr Stem Cell Res Ther, vol. 7, No. 6, p. 407-414.

Secondary Progressive MS (SPMS), National Multiple Sclerosis Society, accessed Jan. 11, 2022, 7 pages.

Primary progressive MS (PPMS), National Multiple Sclerosis Society, accessed Jan. 11, 2022, 7 pages.

Abramsky et al., (1982), Alpha-fetoprotein suppresses experimental allergic encephalomyelitis, J Neuroimmunol, 2(1): 1-7.

Baer, (2014) Adipose-derived mesenchymal stromal/stem cells: An update on their phenotype in vivo and in vitro, World J Stem Cells, 6(3): 256-265.

Ben-Nun et al., (1996) The autoimmune reactivity to myelin oligodendrocyte glycoprotein (MOG) in multiple sclerosis is potentially pathogenic: effect of copolymer 1 on MOG-induced disease, J Neurol., 243(4 Suppl 1): S14-S22.

Bolton et al., (1982) Immunosuppression by cyclosporin A of experimental allergic encephalomyelitis, J Neurol Sci, 56 (2-3): 147-153.

Cohen et al., (2007) Randomized, double-blind, dose-comparison study of glatiramer acetate in relapsing-remitting MS, Neurology, 68(12): 939-944.

Croitoru-Lamoury et al., (2007) Human mesenchymal stem cells constitutively express chemokines and chemokine receptors that can be upregulated by cytokines, IFN-beta, and Copaxone, J Interferon & Cytokine Res, 27(1): 53-64.

Freedman et al., (2010) The therapeutic potential of mesenchymal stem cell transplantation as a treatment for multiple sclerosis: consensus report of the International MSCT Study Group, Mult Scler, 16(4): 503-510.

Johnson et al., (1995) Copolymer 1 reduces relapse rate and improves disability in relapsing-remitting multiple sclerosis.Results of a phase III multicenter, double-blind, placebo-controlled trial, Neurology, 45(7): 1268-1276.

Lin et al., (2012) Is CD34 truly a negative marker for mesenchymal stromal cells?, Cytotherapy 14(10): 1159-1163.

(56) References Cited

OTHER PUBLICATIONS

Riordan et al., (2009) Non-expanded adipose stromal vascular fraction cell therapy for multiple sclerosis, J Transl Med, 7: 29; 9 pages.
Sela et al., (1990) Suppressive activity of Cop-1 in EAE and its Relevance to Multiple Sclerosis, Bull Inst Pasteur, 88: 303-314.
Silva and Ferrari; Animal experimental models for understanding and treating Multiple Sclerosis, SMGroup, Dover, DE 19904, USA. Published: Aug. 18, 2016; 16 pages.
Soleimani et al., (2016) Stem Cell Therapy—Approach for Multiple Sclerosis Treatment, Arch Neurosci, 3(1): e21564; 9 pages.
Teitelbaum et al., (1971) Suppression of experimental allergic encephalomyelitis by a synthetic polypeptide, Eur J Immunol, 1(4): 242-248.
Teitelbaum et al., (1973) Suppression by several synthetic polypeptides of experimental allergic encephalomyelitis induced in guinea pigs and rabbits with bovine and human basic encephalitogen, Eur J Immunol, 3(5): 273-279.
Teitelbaum et al., (1996) Copolymer 1 inhibits chronic relapsing experimental allergic encephalomyelitis induced by proteolipid protein (PLP) peptides in mice and interferes with PLP-specific T cell responses, J Neuroimmunol, 64(2): 209-217.
Traktuev et al., (2008) A population of multipotent CD34-positive adipose stromal cells share pericyte and mesenchymal surface markers, reside in a periendothelial location, and stabilize endothelial networks, Circ Res, 102 (1): 77-85.
ClinicalTrials.gov Identifier: NCT02157064, Outcomes Data of Adipose Stem Cells to Treat Multiple Sclerosis, Sponsor: StemGenex, Retrieved from: https://clinicaltrials.gov/ct2/show/NCT02157064 on Mar. 15, 2017; 3 pages.
Treatment procedure with stem cells. Swiss medica 21, regenerative medicine clinical center, Primary Progresive Multiple Sclerosis—Case 034, Retrieved from: http://www.startstemcells.com/Primary-Progresive-Multiple-Sclerosis-Case034.html on May 8, 2017. 7 pages.
Martino et al., (2010) Stem cell transplantation in multiple sclerosis: current status and future prospects. Nat Rev Neurol 6(5): 247-255.
Ghasemi et al. Transplantation of Human Adipose-Derived Stem Cells Enhances Remyelination in Lysolecithin-Induced Focal Demyelination of Rat Spinal Cord, 2014, Mol Biotechnol 56:470-478.
Choi et al. Cell Proliferation and Neuroblast Differentiation in the Rat Dentate Gyrus After Intrathecal Treatment with Adipose-Derived Mesenchymal Stem Cells 2011 Cell Mol Neurobiol 31:1271-1280.
Ra et al. Stem cell treatment for patients with autoimmune disease by systemic infusion of culture-expanded autologous adipose tissue derived mesenchymal stem cells, 2011 Journal of Translational Medicine 9:181.
Scruggs et al. Age of the Donor Reduces the Ability of Human Adipose-Derived Stem Cells to Alleviate Symptoms in the Experimental Autoimmune Encephalomyelitis Mouse Model Stem Cells Translationalmedicine 2013;2:797-807.
Wolinsky et al. Glatiramer acetate treatment in PPMS: Why males appear to respond favorably Journal of the Neurological Sciences 286 (2009) 92-98.
Aharoni, "Immunomodulation neuroprotection and remyelination—The fundamental therapeutic effects of glatiramer acetate: A critical review", Journal of Autoimmunity, (2014), 54: 81-92.
Aharoni et al., "Immunomodulatory Therapeutic Effect of Glatiramer Acetate on Several Murine Models of Inflammatory Bowel Disease", The Journal of Pharmacology and Experimental Therapeutics, (2006), vol. 318, No. 1, pp. 68-78.
Boismenu and Chen, "Insights from mouse models of colitis", Journal of Leukocyte Biology, (2000), vol. 67(3): 267-278.
Chinnadurai et al., "Challenges in animal modelling of mesenchymal stromal cell therapy for inflammatory bowel disease", World J Gastroenterol (2015), 21(16): 4779-4787.
Flores et al., "Stem cell therapy in inflammatory bowel disease: A promising therapeutic strategy?", World J Stem Cells, (2015), 7(2): 343-351.
Jung et al., "Human adipose-derived stem cells attenuate inflammatory bowel disease in IL-10 knockout mice", Tissue and Cell, (2015), 47(1): 86-93.
Neuhaus et al., "Pharmacokinetics and pharmacodynamics of the interferon-betas, glatiramer acetate, and mitoxantrone in multiple sclerosis", Journal of the Neurological Sciences, (2007), 259(1-2): 27-37.
Panés et al., "852 Cx601, Expanded Allogeneic Adipose-Derived Mesenchymal Stem Cells (eASC), for Complex Perianal Fistulas in Crohn's Disease: Results From a Phase III Randomized Controlled Trial", Gastroenterology, (2016), 150(4): Supplement 1, p. S181.
Shanahan "Inflammatory bowel disease: immunodiagnostics, immunotherapeutics, and ecotherapeutics", Gastroenterology, (2001), 120(3): 622-635.
Todd et al., "Mesenchymal Stem Cells as Vehicles for Targeted Therapies", In: Drug Discovery and Development—Present and Future edited by Izet M. Kapetanovic, IntechOpen, (2011), DOI: 10.5772/29124, pp. 489-528.
Han et al., Adipose-Derived Stromal Vascular Fraction Cells: Update on Clinical Utility and Efficacy, Critical Reviews in Eukaryot Gene Expression, 2015, 25(2): 145-152.

\* cited by examiner

TREATMENT OF MULTIPLE SCLEROSIS WITH ADIPOSE-DERIVED STEM CELLS

CROSS-REFERENCE TO RELATED APPLICATIONS

This application is a 35 U.S.C. § 371 National Stage of International Patent Application No. PCT/IL2018/050523, filed May 14, 2018, designating the United States and claiming priority to U.S. provisional application No. 62/506,006, filed on May 15, 2017. The above identified applications are incorporated by reference.

FIELD OF THE INVENTION

The present invention relates to treatment regimens for multiple sclerosis comprising administration of adipose-derived stem cells. In particular, the invention relates to treatment of progressive forms of multiple sclerosis using intra-ventricular or intrathecal administration of adipose-derived stem cells.

BACKGROUND OF THE INVENTION

Multiple sclerosis (MS) is a chronic inflammatory disease of the central nervous system (CNS) which typically occurs at young adults, more prevalent in women than in men. MS affects the ability of nerve cells in the brain and spinal cord to communicate with each other and control body functions. The clinical disability is linked to an inflammation of myelin, the protective sheath around the axons of the CNS, which is damaged due to an autoimmune attack and neurodegenerative processes. As a consequence, the white matter of the brain and spinal cord becomes scarred by focal lesions (plaques) leading to neurological dysfunction. There are several patterns of symptoms of MS. Most patients experience a relapsing-remitting (RRMS) course at the initial stage, characterized by unpredictable relapses followed by periods of partial or complete recovery (remission), which at some point becomes progressive (PMS). Such progressive MS is classified as secondary progressive MS (SPMS). Some patients experience a progressive course from the onset of symptoms, and such disease pattern is classified as primary progressive MS (PPMS).

Patients with relapsing-remitting MS are typically treated with corticosteroids during acute attacks (relapses), and with immunomodulatory- or immunosuppressive drugs to prevent new relapses and progression of disability. These include interferon beta (Avonex®, Rebif®, Betaseron®), glatiramer acetate (Copaxone®), dimethyl fumarate (Tecfidera®), fingolimod (Gilenya®) natalizumab (Tysabri®) and the chemotherapeutic agent mitoxantrone in more severe cases.

Progressive forms of MS are sometimes treated using similar drugs, but treatment is mainly focused on managing symptoms and rehabilitation. All treatment options for MS are only partially effective.

A recent review highlights that progressive MS is an area where there is currently a paucity of available disease-modifying treatments (Clinical Medicine, 2016, Vol. 16(6), pages s53-s59). Ocrelizumab (OCREVUS™) is a humanized anti-CD20 monoclonal antibody, which was granted Breakthrough Therapy Designation for PPMS by the Food and Drug Administration (FDA) in 2016 (Investor Update by Roche, Basel, Feb. 17, 2016).

Mesenchymal Stem Cells (MSCs) for the Treatment of Autoimmune and/or Neurodegenerative Diseases:

MSCs are a source of multipotent self-renewing cells, originally identified in adult bone marrow. Naturally, they differentiate to produce osteoblasts, chondrocytes and adipocytes. MSCs provide an accessible source of multipotent stem cells alternative to embryonic stem (ES) cells. MSCs potentially circumvent the need for immunosuppression in cellular therapies since they can be derived from an autologous source and also because they are characterized by an immuno-privileged nature advantageous for allogeneic use.

MSCs based therapies have shown to be effective in preclinical studies for a number of indications including graft versus host disease, stroke, myocardial infarction, pulmonary fibrosis and autoimmune disorders. MSCs are also being extensively researched as a therapeutic tool against neurodegenerative diseases. MSCs have been discussed with regard to two aspects in the context of neurodegenerative diseases: their ability to transdifferentiate into neural cells under specific conditions and their neuroprotective and immunomodulatory effects. When transplanted into the brain, MSCs produce neurotrophic and growth factors that protect and induce regeneration of damaged tissue. Additionally, MSCs have also been explored as gene delivery vehicles, for example being genetically engineered to over express glial-derived or brain-derived neurotrophic factor in the brain. Clinical trials involving MSCs are currently underway for MS, ALS, traumatic brain injuries, spinal cord injuries and stroke.

Adipose-Derived Stem Cells (ADSCs):

It has been shown over the past few decades that adipose tissue is in addition to its main function as an energy reservoir also an abundant resource for multipotent stromal cells (Zuk et al., Mol Biol Cell 2002; 13: 4279-4295).

WO 2010/045645 discloses methods of recovering adipose stem cells from adipose tissue.

U.S. Pat. No. 8,021,882 discloses a method for producing stem cell conditioned media for the treatment of neurological insults, by providing a culture of adipose stem cells and collecting the supernatants thereof.

Constantin et al. (2009) *Stem Cells.*, 27(10):2624-35 studied intravenous administration of adipose-derived mesenchymal stem cells to mice in chronic experimental autoimmune encephalomyelitis (EAE).

Stepien et al. (2016) *Mediators of Inflammation*, vol. 2016, report a one-year follow-up of MS patients with RRMS or SPMS treated with autologous adipose stem cell injected intrathecally.

WO 2006/057003 discloses, inter alia, methods of stem cell therapy using bone marrow-derived stem cells in combination with glatiramer.

Aharoni et al. (2009) *J Neuroimmunol.*, 215(1-2):73-83 report about co-treatment of EAE-induced mice with muscle progenitor cells (MPCs), transplanted either intraventricularly or intraperitoneally, and glatiramer acetate.

There is a need in the art for improved methods for treating multiple sclerosis, particularly for patients with progressive forms of the diseases.

SUMMARY OF THE INVENTION

The present invention provides according to some aspects therapies for multiple sclerosis (MS), including progressive MS, particularly primary progressive MS, using adipose-derived stem cells (ADSCs) administered into the central nervous system (CNS). The present invention further provides improved methods for obtaining ADSCs, which are more cost effective and which provide higher yields compared to currently used methods.

The present invention is based, in part, on the surprising effect of human ADSCs administered into the CNS on the clinical score in an animal model of chronic multiple sclerosis. The cells were found to be particularly effective in reducing the maximal disease score and, importantly, in slowing the progression of the disease. Advantageously, the cells were isolated using an improved method as exemplified herein below. The improved method, disclosed herein for the first time, involves freezing and thawing a sample of adipose tissue obtained by lipoaspiration, i.e. a lipoaspirate, before further processing. The improved method also avoids the need for applying a buffer to destroy red blood cells found in the lipoaspirate, as required by currently used methods. The improved method thus also eliminates subsequently separating the ADSCs from cell debris. It was surprisingly found that even though a red blood cell lysis buffer is not applied, the resulting ADSCs sample grows as effectively as a sample isolated according to standard methods.

According to one aspect, the present invention provides a method of treating primary progressive multiple sclerosis comprising administering non-genetically modified human adipose-derived stem cells (hADSCs) into the central nervous system (CNS) of a subject in need thereof.

In some embodiments, the hADSCs are hADSCs obtained from human subcutaneous fat by:
 (a) freezing a lipoaspirate;
 (b) thawing the lipoaspirate and dissociating with a tissue-dissociation enzyme or by mechanical disruption;
 (c) pelleting a cellular fraction comprising the hADSCs by centrifugation, and optionally washing the pellet with a suspension medium capable of supporting cell viability and subjecting the suspension to at least one additional centrifugation;
 (d) resuspending the pellet obtained in step (c) in a suspension medium capable of supporting cell viability and selecting hADSCs from the population of cells in the resuspended pellet;
 (e) optionally conducting at least one filtration prior to the hADSC selection; and
 (f) optionally culturing the hADSCs for at least 3 passages.

In some embodiments, the hADSCs are hADSCs obtained from human subcutaneous fat by: (i) freezing a lipoaspirate; (ii) thawing the lipoaspirate and dissociating with a tissue-dissociation enzyme or by mechanical disruption; (iii) pelleting a cellular fraction comprising the hADSCs by centrifugation; (iv) washing the pellet with an isotonic buffer or culture medium and subjecting to a further centrifugation; (v) resuspending the pellet obtained in step (iv) in an isotonic buffer or culture medium and conducting at least one filtration; (vi) selecting hADSCs from the population of cells in the resuspended pellet; and (vii) culturing the hADSCs for at least 3 passages.

As disclosed herein, the method of obtaining ADSCs avoids the need for applying a buffer to cause lysis of red blood cells originally found in the lipoaspirate. Thus, in some embodiments, the lipoaspirate is processed to isolate adipose-derived stem cells without applying a red blood cells lysis buffer. According to these embodiments, the cellular fraction comprising the hADSCs obtained following centrifugation is not exposed to a red blood cell lysis buffer.

According to another aspect, the present invention provides a method of injecting human adipose-derived stem cells (hADSCs) into the central nervous system (CNS) of a subject in need thereof, the method comprising obtaining hADSCs from human subcutaneous fat by:
 (a) freezing a lipoaspirate;
 (b) thawing the lipoaspirate and dissociating with a tissue-dissociation enzyme or by mechanical disruption;
 (c) pelleting a cellular fraction comprising the hADSCs by centrifugation and optionally washing the pellet with a suspension medium capable of supporting cell viability and subjecting to at least one more centrifugation;
 (d) resuspending the pellet obtained in step (c) in a buffer or culture medium and conducting at least one filtration;
 (e) selecting hADSCs from the population of cells in the resuspended pellet;
 (f) optionally culturing the hADSCs for at least 3 passages; and
 (g) injecting the hADSCs into the CNS of the subject.

According to a further aspect, the present invention provides a method for obtaining human adipose-derived stem cells (hADSCs) from human subcutaneous fat for administration to a subject in need thereof, the method consisting of:
 (a) freezing a lipoaspirate;
 (b) thawing the lipoaspirate and dissociating with a tissue-dissociation enzyme or by mechanical disruption;
 (c) pelleting a cellular fraction comprising the hADSCs by centrifugation, and optionally washing the pellet with a suspension medium capable of supporting cell viability and subjecting the suspension to at least one additional centrifugation;
 (d) resuspending the pellet obtained in step (c) in a suspension medium capable of supporting cell viability and conducting at least one filtration;
 (e) selecting hADSCs from the population of cells in the resuspended pellet; and
 (f) optionally culturing the hADSCs for at least 3 passages prior to their administration to the subject.

As disclosed herein, the cellular fraction comprising the hADSCs obtained following centrifugation is not exposed to a red blood cell lysis buffer.

In some embodiments, the hADSCs are selected by adherence to a cell culture vessel. In some embodiments the cells adhere to a plastic tissue culture vessel.

In some embodiments, freezing is carried out at −80° C. followed by vapor phase liquid nitrogen.

In some embodiments, the tissue-dissociation enzyme is selected from a collagenase, a dispase or a combination thereof. In some specific embodiments, the tissue-dissociation enzyme is a collagenase.

In some embodiments, the hADSCs are characterized by positive expression of CD44, CD73 and CD90 by at least 95% of the cells, positive expression of CD105 by at least 90% of the cells, and negative expression of CD45, CD19, CD11b and HLA-DR by at least 95% of the cells. According to some embodiments, the hADSCs are further characterized by positive expression of CD34 by 1-10% of the cells.

In some embodiments, the hADSCs are characterized by positive expression of CD44, CD73 and CD90 by at least 98% of the cells, positive expression of CD105 by at least 90% of the cells, and negative expression of CD45, CD19, CD11b and HLA-DR by at least 98% of the cells.

In some embodiments, at least 50% of the cells are positive for CD105, CD73, CD44 and CD90, and negative for CD45, CD19, CD11b and HLA-DR.

In some embodiments, the hADSCs are hADSCs cultured to a passage number between 3-10 prior to their administration. In additional embodiments, the hADSCs are hADSCs cultured to a passage number between 3-5 prior to their administration.

In some embodiments, the hADSCs are hADSCs cultured in a xeno-free medium prior to their administration.

According to some embodiments, the hADSCs are administered once.

According to other embodiments, the hADSCs are administered more than once, for example twice, three times, four times, etc. Each possibility represents a separate embodiment of the present invention. According to some embodiments, the hADSCs are administered once every 2-8 months. According to additional embodiments, the hADSCs are administered once every 3-12 months.

According to some embodiments, administering the hADSCs is by intrathecal administration.

According to other embodiments, administering the hADSCs is by intraventricular or intracerebroventricular (ICV) administration, namely into the brain ventricles.

According to some embodiments, the hADSCs are derived from human subcutaneous fat obtained by liposuction aspiration.

According to some embodiments, the hADSCs are autologous.

According to other embodiments, the hADSCs are allogeneic.

According to some embodiments, administering the hADSCs comprises administrating about $10^5$-$3\times10^8$ cells per one administration.

The subject to be treated as described herein is typically a human. According to some embodiments, the methods and compositions of the present invention are useful for the treatment of multiple sclerosis, particularly progressive forms of multiple sclerosis (MS). Thus, according to some embodiments, the subject is suffering from MS. In some embodiments, the subject is a subject suffering from a progressive form of MS. In some specific embodiments, the progressive MS is secondary progressive MS. In additional specific embodiments, the progressive MS is primary progressive MS.

These and further aspects and features of the present invention will become apparent from the detailed description, examples and claims which follow.

DETAILED DESCRIPTION OF THE INVENTION

Figure 1:
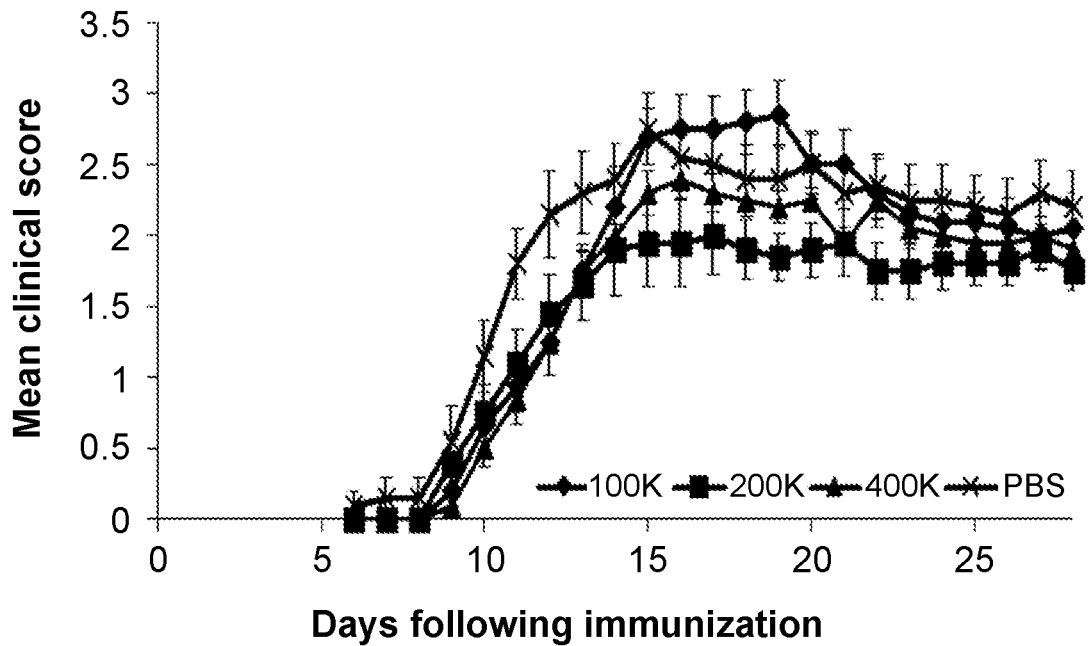
FIG. 1: ADSC dose response on EAE—Mean Clinical Score analysis up to day 28. All groups (n=10/group, +/−standard error).

The present invention provides according to some aspects therapies for multiple sclerosis (MS) including progressive MS using adipose-derived stem cells (ADSCs).

In some embodiments, a method of treating primary progressive multiple sclerosis comprising administering human adipose-derived stem cells (hADSCs) into the central nervous system (CNS) of a subject in need thereof is provided.

The inventors of the present invention have utilized the MOG induced EAE model for evaluation of the effect of adipose-derived mesenchymal stem cells on the disease outcome. MOG is a glycoprotein believed to be important in the process of myelinization of nerves in the central nervous system (CNS) Immunization with MOG 35-55 peptide is generally used for induction of a chronic EAE in C57BL/6 mice. ADSCs were injected into the brain ventricles (ICV) of mice in which EAE has been induced using MOG. Mice were treated with various doses of stem cells.

The surprising observations disclosed herein for the first time demonstrate a clear effect of human ADSCs on chronic EAE, including clinical score, maximum mean disease score and disease progression.

The present invention thus provides treatment methods and regimens comprising administration of human mesenchymal adipose-derived stem cells to subjects suffering from progressive forms of multiple sclerosis. These treatments afford superior therapeutic efficacy for multiple sclerosis, compared to intravenous treatment with stem cells. The current treatment resulted in improved and prolonged effects as determined by various clinical scores.

At present methods and regimens for treatment of multiple sclerosis, comprising administration of adipose-derived stem cells are not yet proven effective and safe, nor are any treatments commercially available. Such therapies would be beneficial to many patients, particularly to those with advanced disease accompanied by neurological symptoms or physical disabilities. Specifically, this treatment will benefit patients with progressive forms of multiple sclerosis.

The term "treating" as used herein refers to prevention, suppression or alleviation of a symptom or of a plurality of symptoms after the onset of primary progressive or secondary progressive multiple sclerosis. In certain embodiments, the symptom is selected from the group consisting of impaired coordination, impaired walking capability, impaired balance, weakness of the leg, stiffness of the leg, impaired memory, impaired cognitive function, a difficulty to swallow, impaired vision, general fatigue, pain, impaired bladder function, impaired bowel function, and any combination thereof. Each possibility represents a separate embodiment of the invention.

In some particular embodiments, treating multiple sclerosis according to the present invention comprises slowing disease progression, i.e., slowing the progression of disability.

The "subject" to which the cells are administered is a mammal, typically a human. The subject according to some embodiments is suffering from a progressive form of multiple sclerosis, namely, diagnosed with a progressive form of multiple sclerosis.

The term "multiple sclerosis" as used herein refers to an auto-immune disease of the central nervous system which is accompanied by one or more of the symptoms described hereinabove. In some embodiments, the progressive MS is secondary progressive MS. In other embodiments, the progressive MS is primary progressive MS. In additional embodiments, the progressive MS is progressive relapsing MS.

According to some embodiments, the ADSCs are administered once. According to some embodiments, the ADSCs are administered multiple times, for example every 2-8 months, every 3-12 months, or less frequent.

According to some embodiments, the ADSCs are administered once every 3, 4, 5, 6, 7, 8, 9, 10, 11, 12 months. Each possibility represents a separate embodiment of the present invention.

Adipose-Derived Stem Cells

The present invention utilizes adipose-derived mesenchymal stem cells. As used herein, the terms "adipose-derived mesenchymal stem cells" or "adipose-derived stem cells", abbreviated "ADSCs" or "hADSCs" (i.e., human adipose-derived stem cells), refer to plastic-adherent, multipotent cell population harvested from adipose tissue. The cell population is characterized by positive expression of CD44, CD73 and CD90 by at least 95% of the cells, positive expression of CD105 by at least 90% of the cells, and negative expression of CD45, CD19, CD11b and HLA-DR by at least 95% of the cells.

In some embodiments, the cell population is characterized by positive expression of CD44, CD73 and CD90 by at least 98% of the cells, positive expression of CD105 by at least 90% of the cells, and negative expression of CD45, CD19, CD11b and HLA-DR by at least 98% of the cells.

The cell population is further characterized by positive expression of CD34 by up to 10%-20% of the cells. In some embodiments, the cell population is characterized by positive expression of CD34 by up to 5% of the cells.

In some embodiments, at least 50% of the cells are positive for CD105, CD73, CD44 and CD90, and negative for CD45, CD19, CD11b and HLA-DR.

According to some embodiments, 90-100% of the human ADSCs are positive for the markers: CD44, CD73 and CD90. According to additional embodiments, at least 95% of the human ADSCs are positive for the markers: CD44, CD73 and CD90. According to yet additional embodiments, at least 98% of the human ADSCs are positive for the markers: CD44, CD73 and CD90.

According to some embodiments, 65-100% of the human ADSCs are positive for CD105. According to additional embodiments, 80-100% of the hADSCs are positive for CD105. According to yet additional embodiments, 90-100% of the hADSCs are positive for CD105. According to yet additional embodiments, 80-95% of the hADSCs are positive for CD105.

According to some embodiments, 0.1-20% of the human ADSCs express the marker CD34. According to additional embodiments, 0.1-10% of the human ADSCs express the marker CD34.

According to other embodiments, 1-10% of the hADSCs are positive for the marker CD34. According to other embodiments, 1-5% of the hADSCs are positive for the marker CD34. According to some embodiments, at least 90% of the cells, for example at least 95% of the cells, are negative for the marker CD34.

According to some embodiments, at least 90% of the administered human ADSCs are negative for the markers: CD45, CD19, CD11b and HLA-DR. According to additional embodiments, at least 95% of the administered human ADSCs are negative for the markers: CD45, CD19, CD11b and HLA-DR. According to yet additional embodiments, at least 98% of the administered human ADSCs are negative for the markers: CD45, CD19, CD11b and HLA-DR.

According to some embodiments, at least 50% of the injected human ADSCs are positive for CD105, CD73, CD44 and CD90, and negative for CD45, CD19, CD11b, and HLA-DR. According to additional embodiments, at least 60%, 70%, 80% or 90% of the injected human ADSCs are positive for CD105, CD73, CD44 and CD90, and negative for CD45, CD19, CD11b and HLA-DR. Each possibility represents a separate embodiment of the invention.

Characterization of cell surface marker expression can be performed by methods known in the art, for example using fluorescence-activated cell sorting (FACS). FACS protocols for FACS are reviewed, for example, in: Flow Cytometry Protocols, Methods in Molecular Biology Volume 699 2011, Editors: Teresa S. Hawley, Robert G. Hawley Humana Press. Exemplary procedures are described below.

Adipose tissue as a source for multipotent stromal/stem cells has several advantages over other sources (Baer P C, Geiger H. *Stem Cells Int* 2012; 2012: 812693). For example, subcutaneous fat is omnipresent in humans and is easily accessible in large quantities by liposuction aspiration. Liposuction is a well-tolerated procedure yielding large quantities of tissue aspirate. The lipoaspirate is typically discarded as medical waste, qualifying it as a good starting material for adipose-derived stromal/stem cell (ASC) isolation. The tissue contains a large number of multipotent cells which can be isolated and proliferated in culture.

According to some embodiments, the ADSCs are derived from human subcutaneous fat. According to particular embodiments, the cells are derived from human subcutaneous fat obtained by liposuction aspiration. The ADSCs may be obtained by liposuction procedures in various areas of the body including stomach, hips, thighs, arms, neck and buttocks. Any procedure of liposuction may be used according to the present invention for obtaining ADSCs, including but not limited to laser, ultrasound and fat removal by abdominoplasty, as known in the art.

The adipose tissue is processed to isolate the adipose-derived stem cells. Preparation methods typically include steps of washing the tissue with buffers such as PBS and saline, and/or with growth media (typically without any additives such as external cytokines or growth factors) e.g. DMEM, StemMACS™ or Plasma-Lyte, and treating the tissue with a tissue-dissociation enzyme such as collagenase and/or subjecting the tissue to non-enzymatic mechanical disruption, for example, using devices such as Tulip Nano Transfer™. Enzymatic digestion of the sample can also be performed using a combination of dispase and collagenase. Liposomes, which are generally aggregated, can be separated from free stromal cells which include the stem cells and other cells such as red blood cells, endothelial cells, and fibroblast cells, by centrifugation. Erythrocytes may be lysed from the suspended pellet using a suitable lysis buffer and the remaining cells can be filtered or centrifuged.

As disclosed herein, an improved method for isolating the adipose-derived stem cells comprises freezing and thawing the adipose tissue prior to further processing. Advantageously, following thawing, the tissue can be processed to isolate the stem cells without the need to apply a lysis buffer to destroy the red blood cells. A standard lysis buffer is typically a solution of ammonium chloride ($NH_4Cl$), potassium bicarbonate ($KHCO_3$) and EDTA at pH 7.3. Such buffer composition selectively lyses red blood cells by exploiting specific characteristics of these cells and their limited ability to withstand osmotic stress.

Freezing according to some embodiments is performed as follows: a lipoaspirate is placed in a freezing bag and DMSO is added at a final concentration of 10%. The freezing bag is placed in a freezing canister and the sample is kept at −80° C. overnight (~24 hours). The frozen sample is then transferred to a vapor phase liquid nitrogen tank. Stability tests can be performed during the storage period.

For thawing, according to some embodiments, the sample is taken out and left at room temperature for a few minutes, typically 5-10 minutes. The sample is then thawed in a water bath at 37° C. for a few minutes, typically between 5-10 minutes, or until most of the sample is thawed. The sample is then washed with a suspension medium capable of supporting cell viability, defined herein as an isotonic buffer or culture medium suitable for mesenchymal stem cells, for example, a buffer, such as PBS, at 37° C. The sample is typically washed twice.

In some embodiments, the process comprises conducting at least one filtration. Filtration is performed, in some embodiments, through a 100 micron mesh and subsequently through a 40 micron mesh in order to further dissociate the tissue and facilitate collection of the SVF fraction.

In order to isolate the ADSCs from within the population of cells in the SVF fraction, processes such as selection by adherence to a cell culture vessel (e.g. by plastic adherence) and/or via beads/antibodies are typically applied. Optionally, cells may be separated by cell sorting or separated immunohistochemically. Bunnell et al. (2008) *Methods.*, 45(2): 115-120, review methods for isolation of ADSCs.

Selection by adherence to the culture vessel is typically carried out by: seeding the SVF cells in a culture flask (e.g. plastic flask) with a suitable culture medium; incubating the seeded cells overnight (in some embodiments for at least 12 hours, or between 24-48 hours); washing the flask to remove non-adherent cells and tissue debris; and adding fresh culture medium to the flask. The adherent cells (ADSCs) may be cultured to a desired level of confluency, following which they may be collected and stored or sub-cultured to further passages.

In some embodiments, the hADSCs are hADSCs obtained from human subcutaneous fat by: (a) freezing a lipoaspirate; (b) thawing the lipoaspirate and dissociating with a tissue-dissociation enzyme or by mechanical disruption; (c) pelleting a cellular fraction comprising the hADSCs by centrifugation, and optionally washing the pellet with a suspension medium capable of supporting cell viability and subjecting the suspension to at least one additional centrifugation; (d) resuspending the pellet obtained in step (c) in a suspension medium capable of supporting cell viability and selecting plastic adherent hADSCs by overnight incubation in plastic flasks; (e) optionally conducting at least one filtration to isolate the hADSCs prior to the plastic adherence selection; and (f) optionally culturing the hADSCs for at least 3 passages.

In some embodiments, the hADSCs are hADSCs obtained from human subcutaneous fat by: (a) freezing a lipoaspirate; (b) thawing the lipoaspirate and digesting with a collagenase; (c) pelleting a cellular fraction comprising the hADSCs by centrifugation and optionally washing the pellet with a buffer or culture medium and subjecting to a further centrifugation; (d) resuspending the pellet obtained in step (c) in a suitable culture medium; and selecting hADSCs by adherence to the cell culture vessel.

In some embodiments, the method for obtaining hADSCs from human subcutaneous fat for administration to a subject in need thereof consists essentially of:

(a) freezing a lipoaspirate;

(b) thawing the lipoaspirate and dissociating with a tissue-dissociation enzyme or by mechanical disruption;

(c) pelleting a cellular fraction comprising the hADSCs by centrifugation, and optionally washing the pellet with a suspension medium capable of supporting cell viability and subjecting the suspension to at least one additional centrifugation;

(d) resuspending the pellet obtained in step (c) in a suspension medium capable of supporting cell viability and conducting at least one filtration;

(e) selecting hADSCs by adherence to the cell culture vessel; and (f) optionally culturing the hADSCs for at least 3 passages prior to their administration to the subject.

An exemplary procedure for isolating ADSCs is described in Example 1 below.

In some preferred embodiments, the ADSCs are cultured before being provided to a subject in need thereof (and/or before being stored for later use). Preferably, the cells are cultured in a xeno-free medium. In some embodiments, the ADSCs are grown to about 80%-100%, confluency for example to about 80% confluency, and sub-cultured to a passage number between 3-10, preferably between 3-5 or 3-4, before administration to the subject. Thus, in some embodiments, the administered cells are at a passage between 3 to 10. In additional embodiments, the administered cells are at passage number between 3 to 5. In some embodiments, the ADSCs are sub-cultured to passage number 3. In some embodiments, the ADSCs are sub-cultured to passage number 4. In some embodiments, the ADSCs are sub-cultured to passage number 5.

Before administration, cells are counted and prepared for injection in a pharmaceutically acceptable diluent/carrier. Typically, the cells are concentrated before administration to the subject. The concentration typically ranges from $1.5 \times 10^4$/ml to $100 \times 10^6$/ml.

A stem cell composition for single administration according to the methods of the present invention comprises, in some embodiments, $10^5$-$3 \times 10^8$ human ADSCs. According to some embodiments, the composition comprises $10^5$-$10^8$ human ADSCs. According to additional embodiments, $10^6$-$10^7$ human ADSCs are injected in one administration. According to yet additional embodiments, $200 \times 10^6$-$300 \times 10^6$ human ADSCs are injected in one administration. According to yet additional embodiments, $10^7$-$2 \times 10^8$ human ADSCs are injected in one administration.

According to some embodiments, the ADSC composition of the present invention is for use by systemic administration. Typically, the administration is into the central nervous system (CNS) of a subject. Such administration may be aimed at bypassing the blood brain barrier. According to yet other embodiments, the ADSCs are administered directly to a specific region of the brain.

According to some embodiments, the composition is administered to the CNS, for example, by intraspinal administration. According to some embodiments, the composition is administered intrathecally. According to other embodiments, the composition is administered by intraventricular or intracerebroventricular (ICV) route, namely into the brain ventricles.

Intraventricular drug delivery is the delivery of medication within the cerebrospinal fluid of the cistern (C1-2 vertebra) and intracranial ventricles. By administering medication directly, less medication is needed, and fewer side effects are seen than with orally administered drugs. The medicine is typically delivered through an implanted catheter connected to a pump, as known in the art. The pump may be programmable, and either implanted or external.

Intrathecal administration is a route of administration for drugs via an injection into the spinal canal, more specifically into the subarachnoid space so that it reaches the cerebrospinal fluid (CSF) and is useful in spinal anesthesia, chemotherapy, or pain management applications. This route is also used to introduce drugs that fight certain infections, particularly post-neurosurgical. The drug needs to be given this way to avoid the blood brain barrier. Intrathecal and epidural drug delivery comprise the intraspinal routes of drug administration. Each route delivers drug to the cerebrospinal fluid (CSF). Intrathecal delivery involves the direct injection of the drug into the CSF within the intrathecal space of the spinal column, whereas drugs injected in the epidural space have to cross the dura membrane in order to reach the CSF. As such, epidurally administered drugs can also reach the systemic circulation whereas intrathecally administered drugs are confined within the CSF circulating in the spinal column and the brain ventricles.

Also encompassed by the present invention is a combination therapy of adipose-derived stem cells and optionally at least one other active agent.

Active agents within the scope of the present invention include, but are not limited to interferons, e.g. pegylated or non-pegylated α-interferons, or β-interferons, e.g. interferon β-1a or interferon β-1b, or τ-interferons; immunosuppressants with optionally antiproliferative/antineoplastic activity, e.g. mitoxantrone, methotrexate, azathioprine, cyclophosphamide, or steroids, e.g. methylprednisolone, prednisone or dexamethasone, or steroid-secreting agents, e.g. ACTH; adenosine deaminase inhibitors, e.g. cladribine; IV immunoglobulin G (e.g. as disclosed in Neurology, 1998, May 50(5):1273-81) monoclonal antibodies to various T-cell surface markers, e.g. natalizumab (ANTEGREN®) or alemtuzumab; TH2 promoting cytokines, e.g. IL-4, IL-10, or compounds which inhibit expression of TH1 promoting cytokines, e.g. phosphodiesterase inhibitors, e.g. pentoxifylline; antispasticity agents including baclofen, diazepam, piracetam, dantrolene, lamotrigine, rifluzole, tizanidine, clonidine, beta blockers, cyproheptadine, orphenadrine or cannabinoids; AMPA glutamate receptor antagonists, e.g. 2,3-dihydroxy-6-nitro-7-sulfamoylbenzo(f)quinoxaline, [1,2,3,4-tetrahydro-7-morpholin-yl-2,3-dioxo-6-(trifluoromethyl)quinoxalin-1-yl]methylphosphonate, 1-(4-aminophenyl)-4-methyl-7,8-methylene-dioxy-5H-2,3-benzodiazepine, or (-)1-(4-aminophenyl)-4-methyl-7,8-methylenedioxy-4,5-dihydro-3-methylcarbamoyl-2,3-benzodiazepine; inhibitors of VCAM-1 expression or antagonists of its ligand, e.g. antagonists of the α4β1 integrin VLA-4 and/or α-4-β-7 integrins, e.g. natalizumab (ANTEGREN®); anti-macrophage migration inhibitory factor (Anti-MIF); xii) Cathepsin S inhibitors; xiii) mTor inhibitors. Each possibility represents a separate embodiment of the invention. Currently preferred one other active agent is FTY720 (2-amino-2-[2-(4-octylphenyl) ethyl] propane-1, 3-diol; fingolimod) belonging to the class of immunosuppressants.

The invention encompasses the combination of ADSCs, with at least one additional drug, preferably, an immunosuppressant, particularly fingolimod.

The present invention also provides use in the treatment of multiple sclerosis of human ADSCs, optionally together with an additional drug being suitable for the treatment of multiple sclerosis.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1—Effect of Human Adipose Derived Stem Cells (hADSCs) on MOG-Induced Chronic EAE in C57BL/6 Mice Materials and Methods ADSCs Isolation:

Lipoaspirate obtained from human healthy donors was frozen at −80° C. and then in vapor phase liquid nitrogen (for over a week). The lipoaspirate was then thawed and washed twice with an equal volume of PBS at 37° C. The lipoaspirate was then digested with collagenase (NB4, Serva) at 37° C. for 35 minutes with shaking. An equivalent volume of DMEM was added and the sample span down once at RT, 300-500 g, for 10 min. The precipitated fraction was washed with DMEM, span down again and the pellet resuspended in culture medium (StemMACS™, Miltentyi), without applying red blood cells lysis buffer. The amount of culture medium was calculated as follows: 50 ml for every 150 ml of initial lipoaspirated tissue. The sample was then filtered through a 100 μm filter, followed by the addition of additional 5 ml medium and centrifugation at 500 g for 10 minutes at RT. The procedure was repeated with a 40 μm filter and the cells were counted. The resulting cells are referred as stromal vascular fraction (SVF).

Cell Culture:

The SVF fraction was plated at a density of ~2×10$^6$ cells per 75 cm$^2$ without any coating and incubated overnight to select for plastic adherent cells (ADSCs). The next day the flask was washed to remove non-adherent cells and tissue debris, fresh medium was added, and the cells were grown to 80-100% confluency, trypsinized and sub-cultured up to passage 3-5.

Cells were then collected and analyzed for the markers: CD105, CD73, CD90, CD45, CD44, CD19, CD11b, HLA-DR and CD34. The cells were stored frozen in liquid nitrogen until use. For use, frozen cells were thawed and plated at a concentration of 5000 cells/cm$^2$ and incubated overnight.

Prior to cells ICV injection the cells were trypsinized, counted and prepared for injection at the selected concentration detailed in Table 2 below and kept on ice until use for a period no longer than 30 min ICV injection was performed using a stereotactic system and care was taken not to injure the mice brain.

Animals:

All animal studies were approved by local ethics committees. C57BL/6 female mice, 7-9 weeks old were randomized into control or treatment groups with similar mean weight Animals were given food and water ad libitum throughout the experiment.

Induction of Experimental Autoimmune Encephalomyelitis (EAE):

In order to induce EAE, an emulsion of myelin-oligodendrocyte-glycoprotein (MOG) 35-55 (GL Biochem co. Ltd, Shanghai, China) in modified Complete Freund's Adjuvant (CFA) (Sigma-Aldrich, St. Louis, Mo., USA) was prepared as follows: heat-killed *M. tuberculosis* strain H37RA (Sigma) was added to CFA reaching a final concentration of 4 mg/mL. Subsequently, 2 mg/mL MOG 35-55 were emulsified with an equal amount of modified CFA. EAE had been induced by injection of this emulsion subcutaneously (SC) on the shaved back of the mouse at one site, followed by an intraperitoneal injection of *Bordetella pertussis* toxin (Sigma) in PBS on Day 0, and 48 hours post MOG immunization.

Measurements:

Body weight was measured daily from Day 0 to Day 29. EAE was assessed by clinical scoring of the mice once daily from Day 0 to Day 29 post-immunization (Table 1). Dead animals (if occur) received a clinical score of 5 and the last weight measurement before animal death was recorded as final weight.

TABLE 1

EAE Clinical Score

| Score | Clinical Signs |
|---|---|
| 0 | Normal mouse; no overt signs of disease |
| 1 | Limp tail |
| 2 | Hind limb paralysis |
| 3 | Hind and front limb paralysis |
| 4 | Complete paralysis: sacrifice for humane reasons |
| 5 | Moribund state; Death by EAE |

The following calculations were derived from clinical score raw data:

Mean maximum score:

is the mean of the highest scores noted for each mouse in a specific group up to an indicated day of analysis.

Mean disease duration:

$$\frac{\text{sum of (day of analysis} - \text{day of disease onset for each mouse)}}{\text{(number of mice per group)}}$$

Mean day of onset:

$$\frac{\text{sum of day of disease onset of each mouse}}{\text{number of mice per group}}$$

Area under the curve (AUC) of clinical score:

calculated using Microsoft Excel and represents disease burden.

Experimental Design:

The experimental design of the EAE model is detailed in Table 2 (n=10 in each group).

TABLE 2

Experimental design

| Group (test article) | Route | Cell Dose (number of cells) | Days of administration | Vehicle, injection volume |
|---|---|---|---|---|
| Control/Vehicle (PBS) | ICV | 0 | 0 | PBS 4 ul |
| ADSCs 100K | ICV | $1 \times 10^5$ | 0 | PBS 4 ul |
| ADSCs 200K | ICV | $2 \times 10^5$ | 0 | PBS 4 ul |
| ADSCs 400K | ICV | $4 \times 10^5$ | 0 | PBS 4 ul |

Statistical Analysis:

Each data set was analyzed using single-factor analysis of variance (ANOVA) followed by two-tailed, two-sample students' T test assuming unequal variances, n=10/group, +/−standard error.

Results

The results of the trial, calculated up to 28 days from the first injection of the test articles, are described in Table 3 and FIGS. 1-6.

Phenotype of the Cells:

| Marker (dye) | % expression |
|---|---|
| CD73 (PE*) | 100 |
| CD90 (PE) | 100 |
| CD105 (PE) | 100 |
| CD44 (FITC**) | 100 |
| HLA-DR (PE) | 0.1 |
| CD34 (PE) | 1.5 |
| CD45 (PE) | 0.5 |
| CD11b (PE) | 0.2 |
| CD19 (PE) | 0.1 |
| IgG1 (PE) | 0.2 |
| IgG2a (PE) | 0.1 |
| IgG1 (FITC) | 0 |

TABLE 3

Effect of ADSCs on EAE

| Groups | AUC Clinical Score | Maximum Mean Disease Score | Mean Day of Onset | Survival Rate at Day 28 |
|---|---|---|---|---|
| Control/Vehicle (PBS) | 36.05 ± 3.33 | 2.90 ± 0.19 | 11.30 ± 0.42 | 100% |
| ADSCs 100K | 33.45 ± 2.78 | 3.00 ± 0.20 | 12.40 ± 0.54 | 100% |
| ADSCs 200K | 26.95 ± 3.13 | 2.35 ± 0.18 | 12.70 ± 0.80 | 100% |
| ADSCs 400K | 29.38 ± 1.12 | 2.6 ± 0.10 | 12.50 ± 0.43 | 100% |

Figure 2:
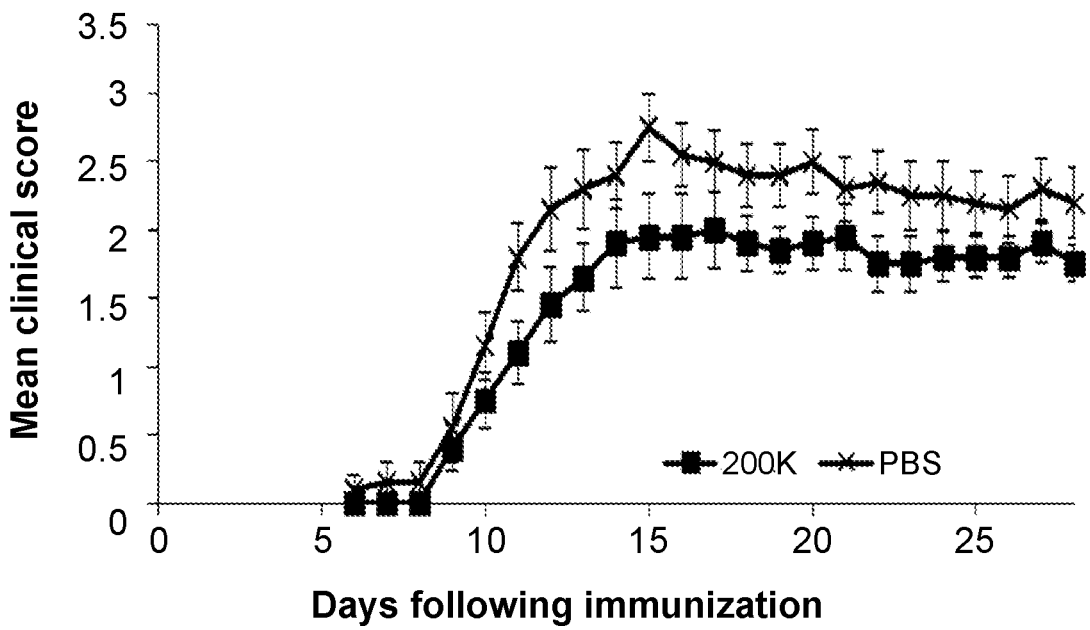
FIG. 2: ADSC dose response on EAE—Mean Clinical Score analysis up to day 28. Vehicle compared to $2\times10^5$ cell/animal. (n=10/group, +/−standard error).
Figure 3:
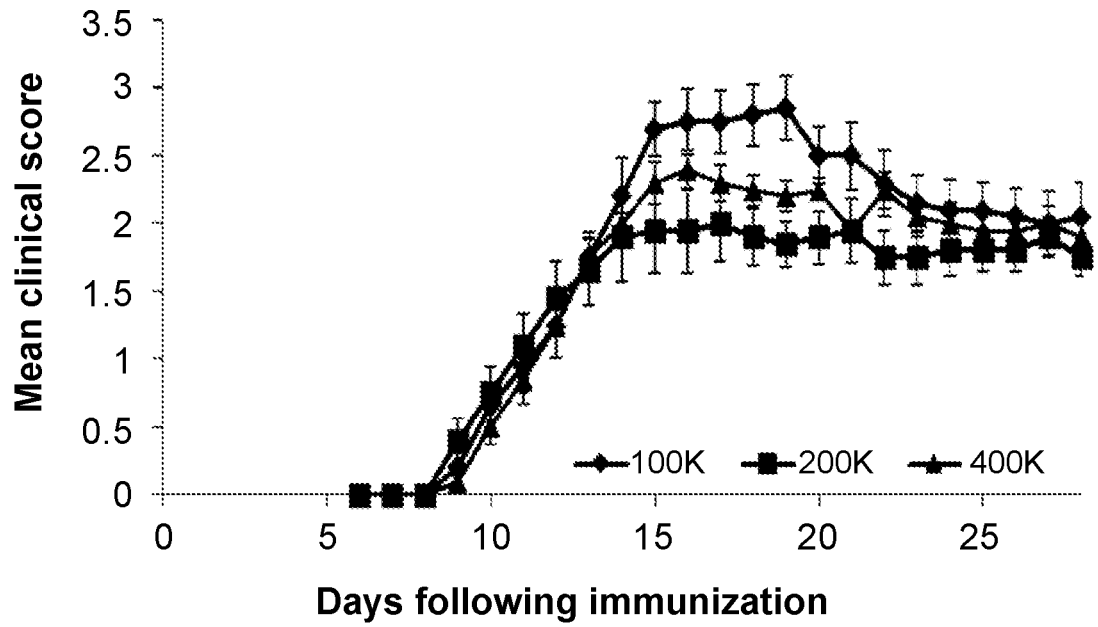
FIG. 3: ADSC dose response on EAE—Mean Clinical Score analysis up to day 28. Comparison of $1\times10^5$ cells, $2\times10^5$ cell, and $4\times10^5$ cells/animal (n=10/group, +/−standard error).

The ICV transplantation of ADSCs in an EAE MOG model showed a decrease in the rate of appearance of the symptoms of the disease at all of the three dosages studied (FIG. 1). The most effective dose was $2 \times 10^5$ cells/animal that showed a significant reduction in the severity of the disease, reaching a plateau at a Mean Clinical Score of 2±0.11, as compared to 2.75±0.25 for the vehicle group (FIG. 2). One-hundred thousand ($1 \times 10^5$) cells per mice did not seem to be enough to elicit changes in progression of the disease and the behavior of the animals was similar to the vehicle control group. As is observed in FIG. 3, the highest dose ($4 \times 10^5$ cells/animal), although effective in the reduction of the symptoms, is less effective than the middle dose of $2 \times 10^5$ cell/animal, probably due to a high density of the cells in the small ICV space of mice.

Figure 4:
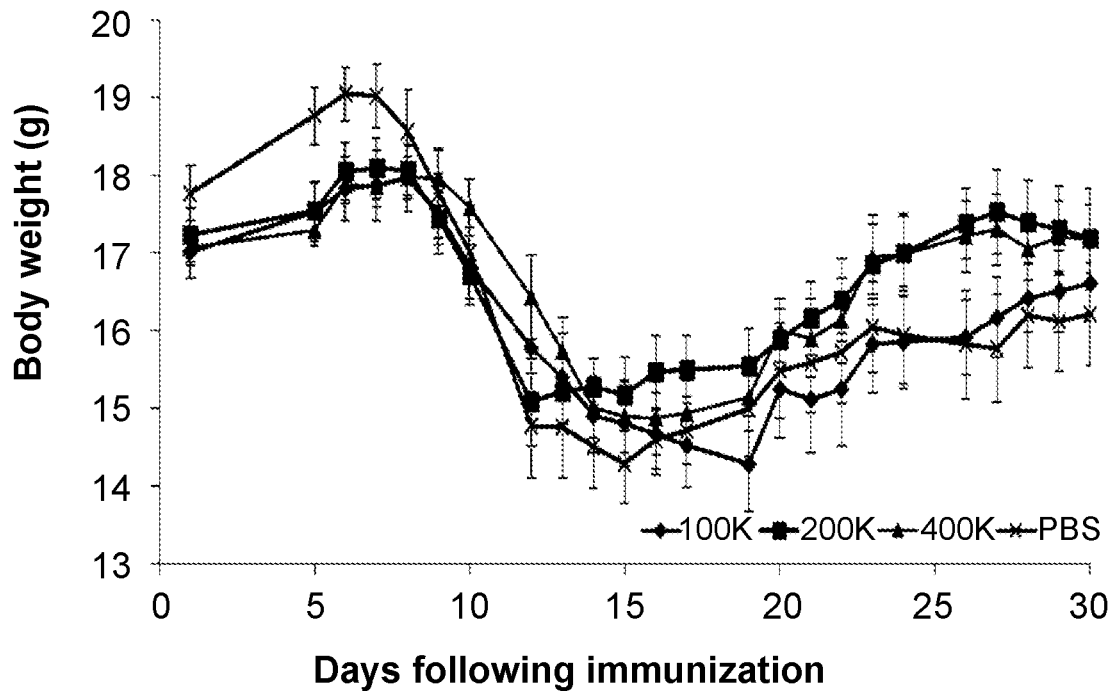
FIG. 4: ADSC dose response on EAE—Weight analysis up to day 29. (n=10/group, +/−standard error).

Analysis of the body weight of the animals confirmed the observation noted in the analysis of the clinical score of the animals. The two higher dosages of the cells ($2\times10^5$ and $4\times10^5$ cells/animal) resulted in a higher average body weight, which was preserved throughout the experiment (FIG. 4).

Figure 5:
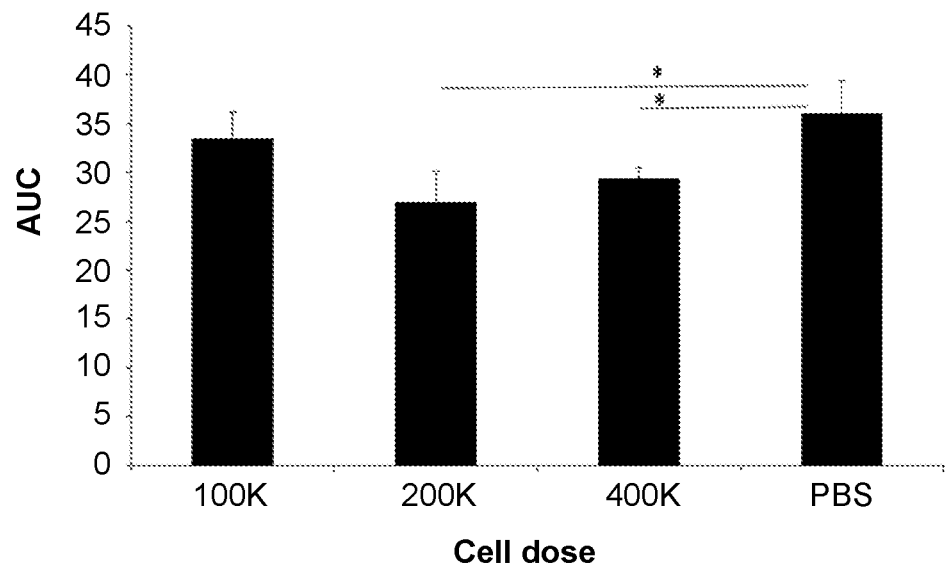
FIG. 5: Effect of ADSCs cell dose on EAE—Mean AUC of Mean Clinical Score (disease burden) up to day 28. *$P<0.05$ (n=10/group, +/−standard error)
Figure 6:
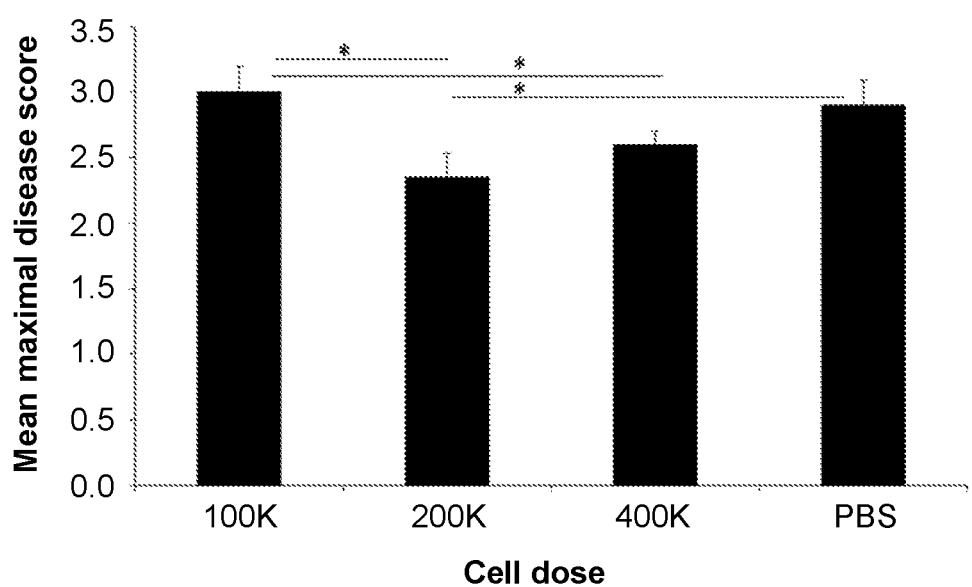
FIG. 6: Effect of ADSCs dose on EAE—Mean Maximum Score analysis up to day 28. *$P<0.05$ (n=10/group, +/−standard error).

The area under the curve (AUC) of Mean Clinical Score calculated as a function of cell dose at day 28 post immunization was significantly lower for the $2\times10^5$ ADSCs and $4\times10^5$ ADSCs animal groups compared to the vehicle and to $1\times10^5$ ADSC (FIG. 5). Furthermore, the Mean Maximal Disease Score in the $2\times10^5$ ADSCs group at day 28 post immunization was significantly lower than that of the $1\times10^5$ ADSCs and the control group (FIG. 6).

The experimental data show a clear advantage of the ICV transplantation of ADSC with a maximum effect at $2\times10^5$ cells per mice. This ADSC dose yielded a long term effect on the attenuation of EAE symptoms that led to a significant reduction of disease burden.

Example 2—Analyses of Cell Surface Markers of ADSCs

Figure 7:
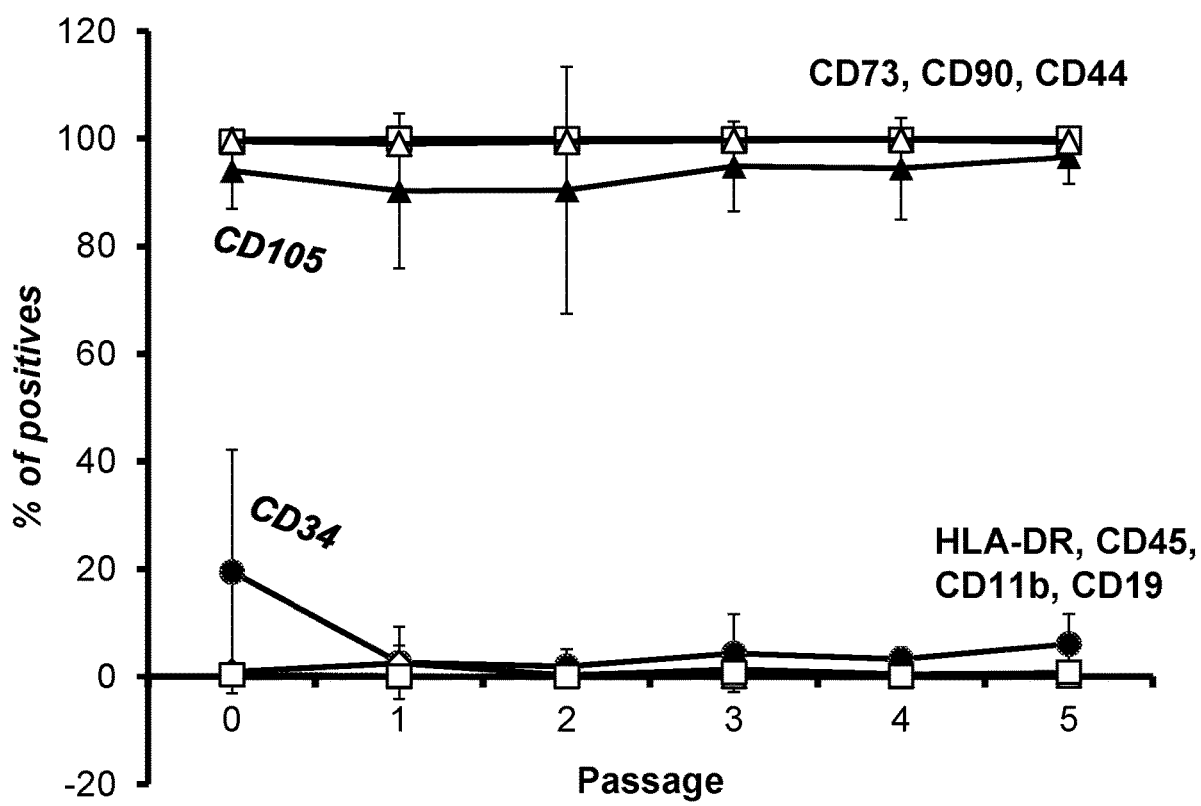
FIG. 7: Cell surface marker expression of ADSCs as a function of passage number. The cells were isolated from adipose tissue and cultured as described in the Examples section, and analyzed for the expression of the indicated markers. The results are the average+/−standard deviation of nine (9) samples.
Figure 8A:
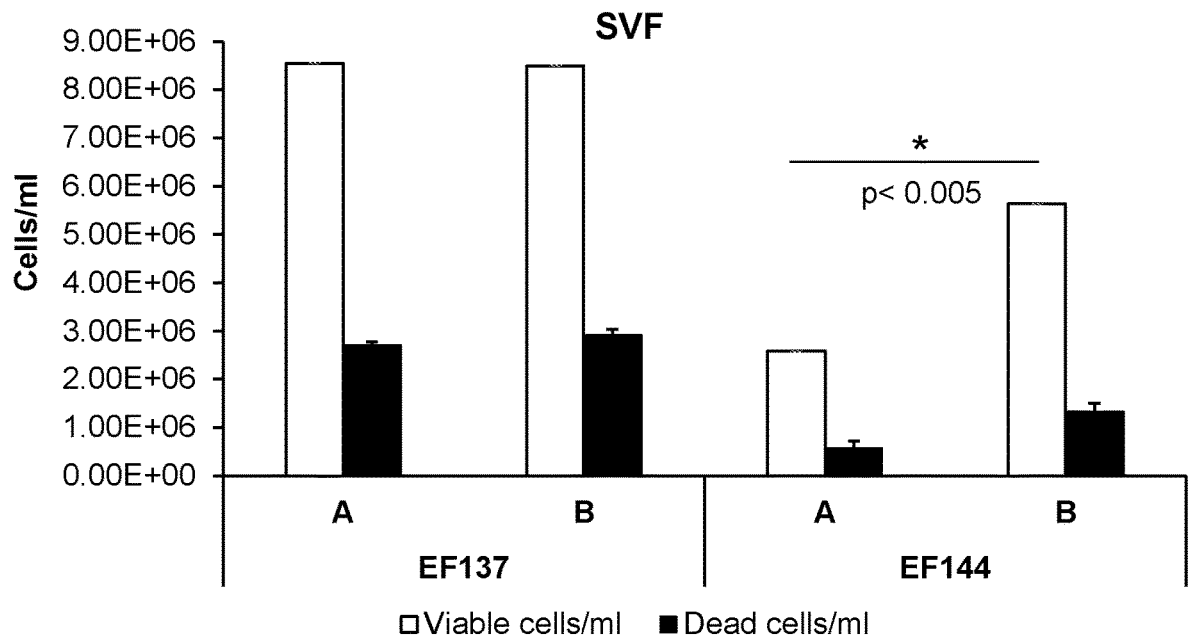
FIG. 8: SVF cell counting data following isolation with or without red blood cell lysis. (A) cells/ml; (B) % viability.
Figure 8B:
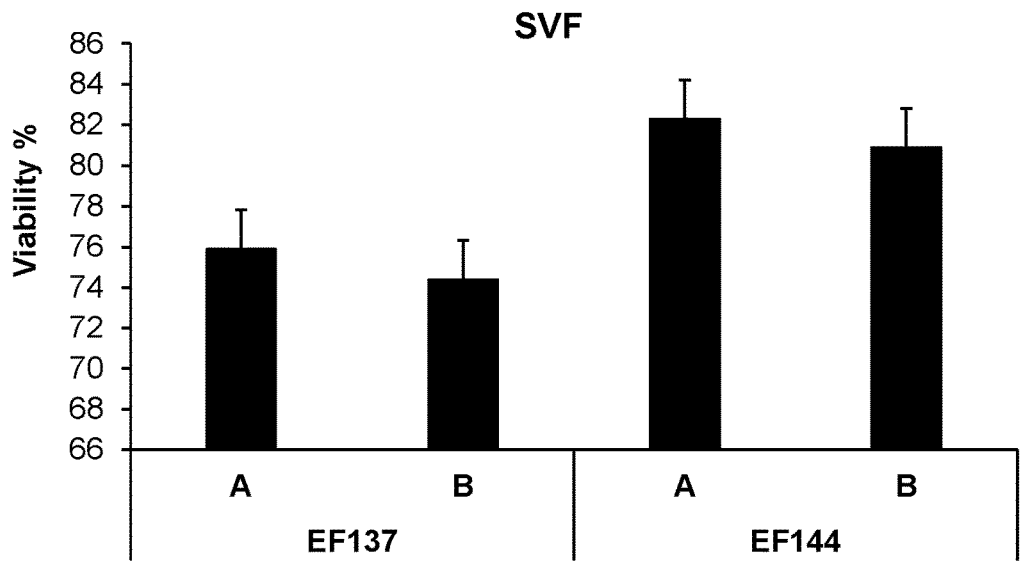
Figure 9A:
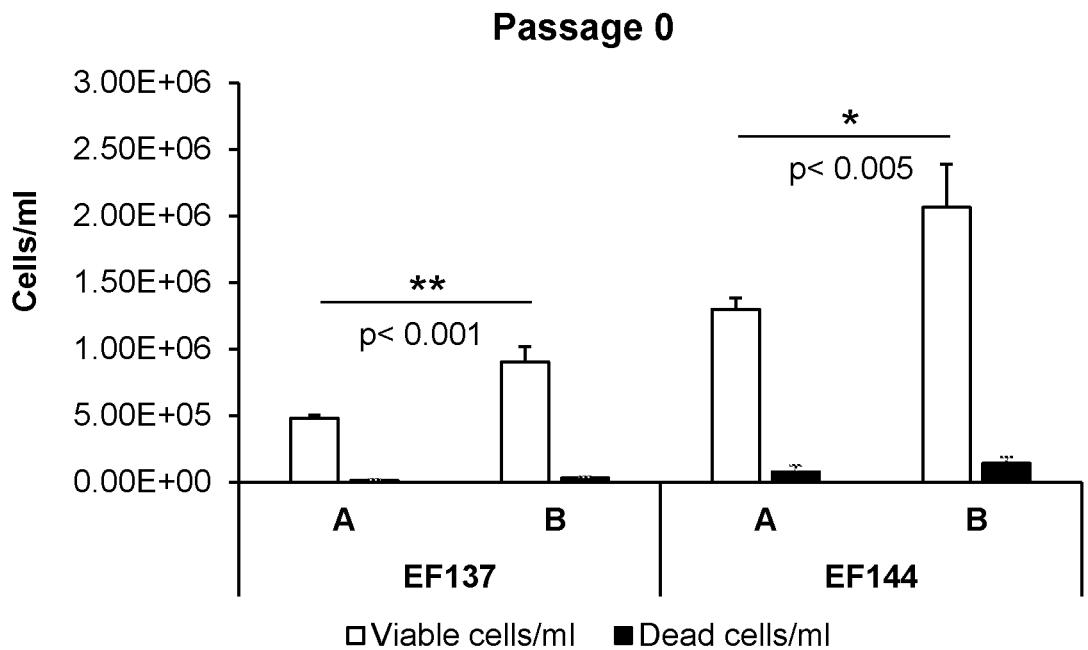
FIG. 9: Cell counting data at passage 0 following isolation with or without red blood cell lysis. (A) cells/ml; (B) % viability.
Figure 9B:
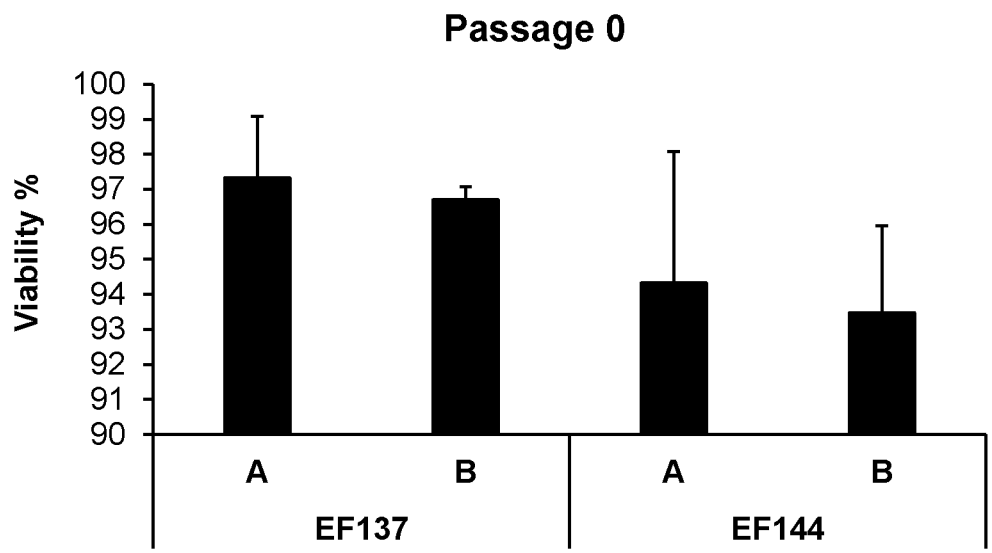
Figure 10A:
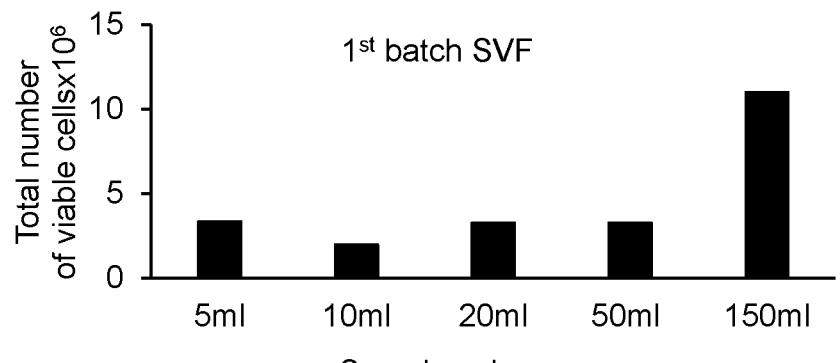
FIG. 10: SVF and ADSC yields as a function of initial volume of lipoaspirated tissue sample—$1^{st}$ batch. Total number of viable cells immediately after SVF isolation (A), at P #0 (B), and at P #1 (C).
Figure 10B:
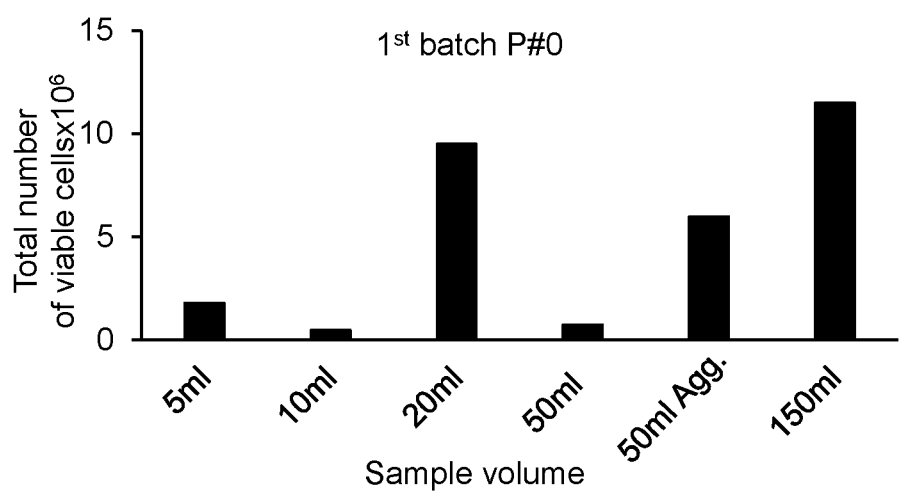
Figure 10C:
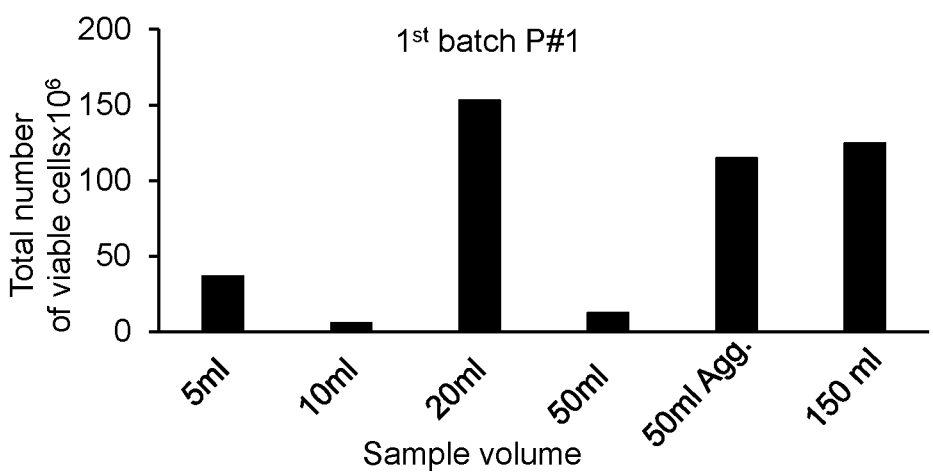
Figure 11A:
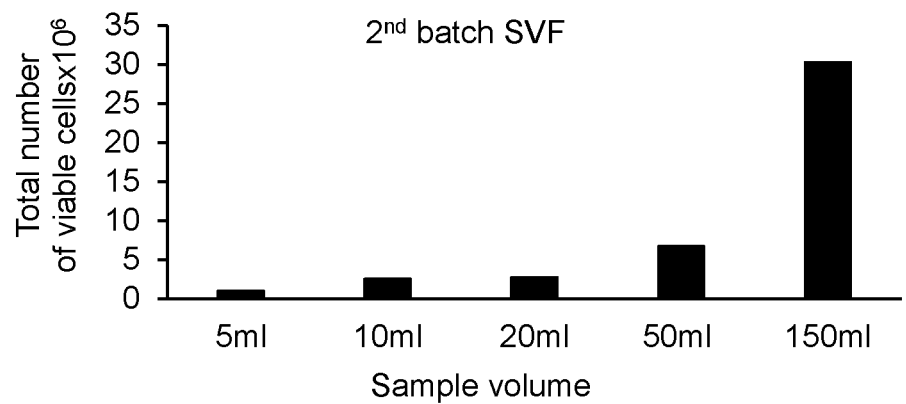
FIG. 11: SVF and ADSC yields as a function of initial volume of lipoaspirated tissue sample—$2^{nd}$ batch. Total number of viable cells immediately after SVF isolation (A), at P #0 (B), and at P #1 (C).
Figure 11B:
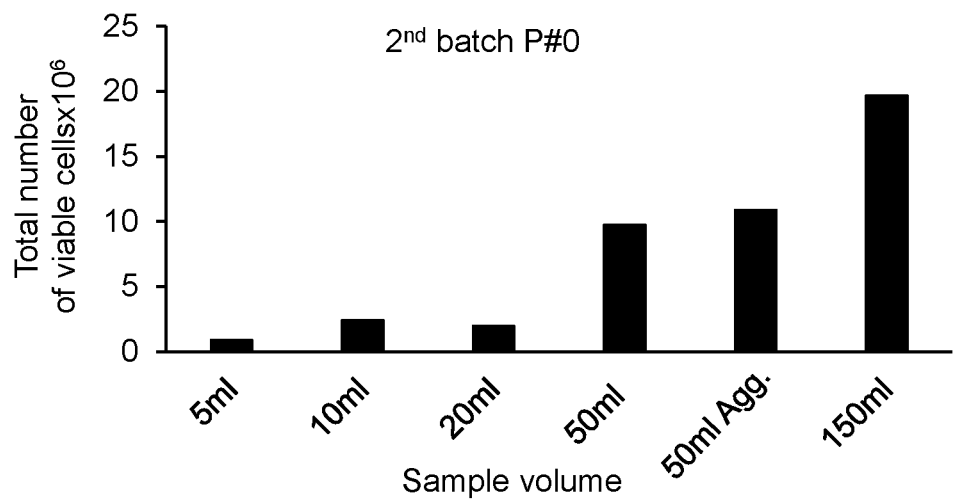
Figure 11C:
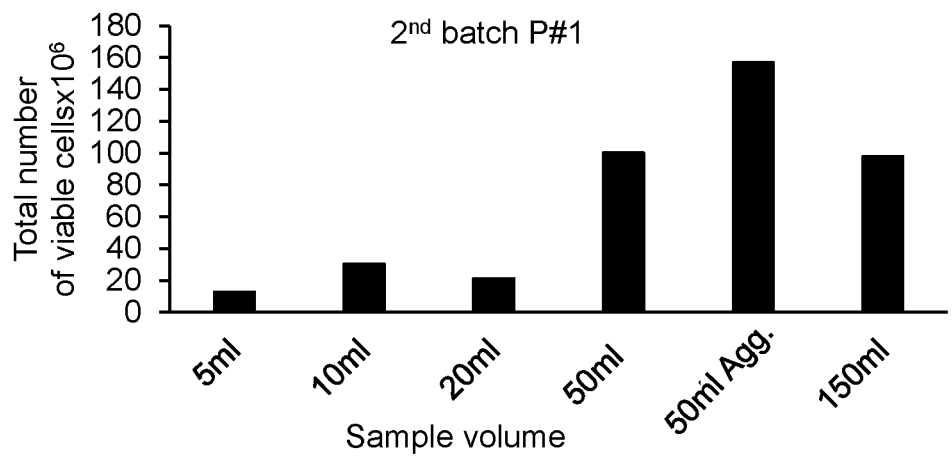
Figure 12A:
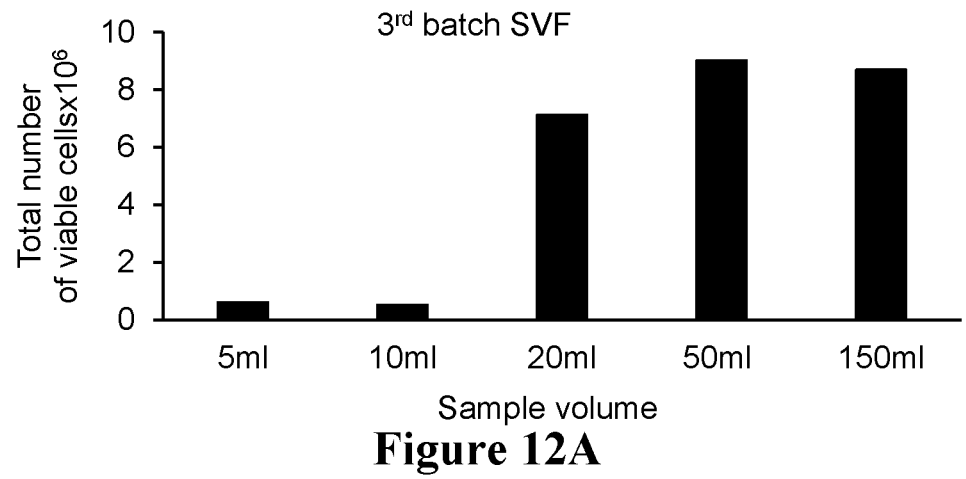
FIG. 12: SVF and ADSC yields as a function of initial volume of lipoaspirated tissue sample—$3^{rd}$ batch. Total number of viable cells immediately after SVF isolation (A), at P #0 (B), and at P #1 (C).
Figure 12B:
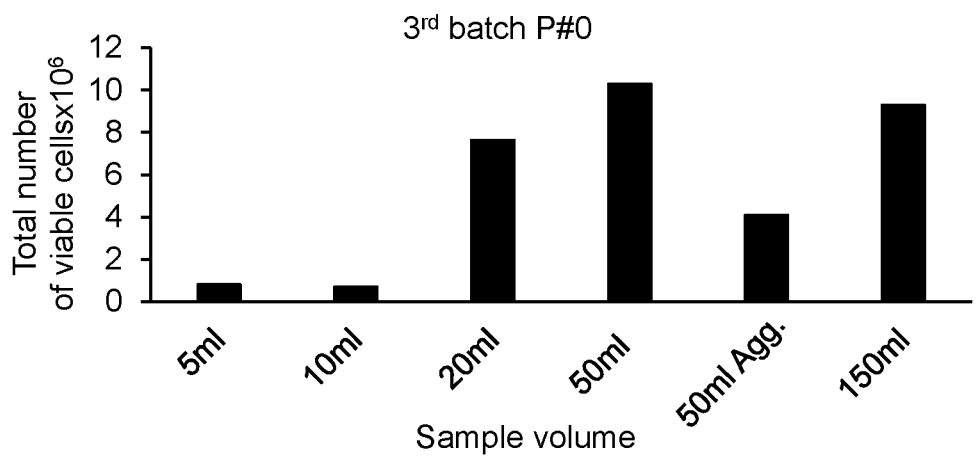
Figure 12C:
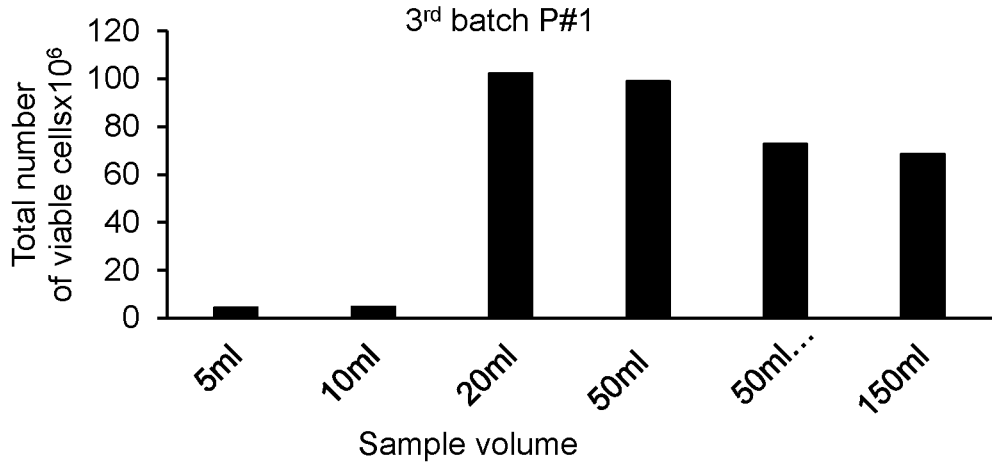

Tables 4-12 summarize FACS analyses of nine (9) samples of ADSCs prepared as described in Example 1 above, following 1-5 passages. Tables 13-14 and FIG. 7 show the average and standard deviation ("StDev") values. As can be seen in the tables and figure, the markers are stabilized after P3. Passage numbers P3-P4 are equivalent to no more than approximately 14 population doublings.

TABLE 4

| | Marker (dye) | Passage 0 | 1 | 2 | 3 | 4 | 5 | |
|---|---|---|---|---|---|---|---|---|
| Sample 1 | CD73 (PE*) | 99.1 | 99.9 | 99.9 | 99.9 | 99.9 | 99.9 | Positives |
| | CD90 (PE) | 97 | 99.9 | 99.9 | 99.9 | 99.9 | 100 | |
| | CD105 (PE) | 90.4 | 78.3 | 97.8 | 89 | 82.1 | 99.7 | |
| | CD44 (FITC**) | 99.6 | 99.8 | 99.9 | 99.9 | 99.7 | 99.8 | |
| | HLA-DR (PE) | 1.2 | 0.2 | 0.1 | 0.1 | 0.4 | 0.1 | Negatives |
| | CD34 (PE) | 14.6 | 0.3 | 0.2 | 0.2 | 1.2 | 10.8 | |
| | CD45 (PE) | 1.5 | 0.1 | 0.1 | 0 | 0.1 | 0.4 | |
| | CD11b (PE) | 1.6 | 0.1 | 0 | 0 | 0 | 0 | |
| | CD19 (PE) | 0.3 | 0.1 | 0 | 0 | 0 | 0.2 | |
| | IgG1 (PE) | 0.3 | 0 | 0.1 | 0 | 0.1 | 0 | Controls |
| | IgG2a (PE) | 0.3 | 0.1 | 0.1 | 0 | 0 | 0 | |
| | IgG1 (FITC) | 0.3 | 0 | 0 | 0 | 0 | 0.1 | |

*PE—Phycoerythrin
**FITC—Fluorescein isothiocyanate

TABLE 5

| | Marker (dye) | Passage 0 | 1 | 2 | 3 | 4 | 5 | |
|---|---|---|---|---|---|---|---|---|
| Sample 2 | CD73 (PE) | 99.9 | 100 | 100 | 100 | 100 | 100 | Positives |
| | CD90 (PE) | No data | 100 | 99.9 | 100 | 99.9 | 100 | |
| | CD105 (PE) | 79.5 | 76.3 | 98.8 | 98.1 | 99.6 | 97.3 | |
| | CD44 (FITC) | 99.2 | 99.2 | 99.9 | 99.4 | 99.7 | 99.4 | |
| | HLA-DR (PE) | 0.3 | 0.1 | 0.1 | 0 | 0.1 | 0.2 | Negatives |
| | CD34 (PE) | 0.4 | 0.3 | 0.4 | 1.4 | 3.1 | 5 | |
| | CD45 (PE) | 0.2 | 0 | 0.1 | 0.1 | 0.1 | 0.4 | |
| | CD11b (PE) | 0.1 | 0 | 0 | 0 | 0 | 0.1 | |
| | CD19 (PE) | 0.1 | 0 | 0 | 0 | 0.1 | 0.4 | |
| | IgG1 (PE) | 0.1 | 0.1 | 0 | 0 | 0 | 0.1 | Controls |
| | IgG2a (PE) | 0.1 | 0.1 | 0 | 0.1 | 0 | 0 | |
| | IgG1 (FITC) | 1 | 0 | 0 | 0 | 0 | 0 | |

TABLE 6

| | Marker (dye) | Passage 0 | 1 | 2 | 3 | 4 | 5 | |
|---|---|---|---|---|---|---|---|---|
| Sample 3 | CD73 (PE) | 99.8 | 100 | 100 | 100 | 100 | 100 | Positives |
| | CD90 (PE) | 99.9 | 100 | 99.9 | 99.9 | 100 | 100 | |
| | CD105-PE | 90.8 | 99.9 | 98.3 | 99.4 | 99.3 | 86.9 | |
| | CD44 (FITC) | 99.4 | 99.9 | 99.8 | 99.5 | 99.6 | 95.9 | |
| | HLA-DR (PE) | 0.7 | 0.1 | 0 | 0 | 0.1 | 0.1 | Negatives |
| | CD34 (PE) | 21.4 | 5 | 1.4 | 6.8 | 7 | 2.3 | |
| | CD45 (PE) | 0.5 | 20.4 | 0.1 | 0.1 | 2.2 | 1.2 | |
| | CD11b (PE) | 0.2 | 0.2 | 0 | 0 | 0.2 | 0 | |
| | CD19 (PE) | 0.2 | 0.3 | 0 | 0 | 0.1 | 0.1 | |

TABLE 6-continued

|  | | Passage | | | | | |
|---|---|---|---|---|---|---|---|
| Marker (dye) | 0 | 1 | 2 | 3 | 4 | 5 | |
| IgG1 (PE) | 0.2 | 0.1 | 0 | 0 | 0.1 | 0 | Controls |
| IgG2a (PE) | 0.2 | 0.1 | 0 | 0 | 0.1 | 0 | |
| IgG1 (FITC) | 0.1 | 0 | 0 | 0.1 | 0 | 0 | |

TABLE 7

| | Marker (dye) | Passage | | | | | | |
|---|---|---|---|---|---|---|---|---|
| | | 0 | 1 | 2 | 3 | 4 | 5 | |
| Sample 4 | CD73 (PE) | 99.9 | 99.9 | 99.9 | 100 | 99.9 | 99.9 | Positives |
| | CD90 (PE) | 99.9 | 99.9 | 99.9 | 99.9 | 99.9 | 99.9 | |
| | CD105 (PE) | 99.4 | 96.9 | 99.1 | 99.6 | 99.9 | 99.9 | |
| | CD44 (FITC) | 99.3 | 98 | 99.5 | 99.5 | 99.4 | 99.8 | |
| | HLA-DR (PE) | 0.2 | 0 | 0.2 | 0 | 0.1 | 0.4 | Negatives |
| | CD34 (PE) | 13.6 | 4.8 | 3.3 | 23.1 | 4 | 1.9 | |
| | CD45 (PE) | 0.7 | 0.1 | 0.2 | 9.7 | 0.3 | 0.2 | |
| | CD11b (PE) | 0.2 | 0 | 0 | 0.1 | 0.4 | 0.2 | |
| | CD19 (PE) | 0.8 | 0 | 0.1 | 5.7 | 0.5 | 3.5 | |
| | IgG1 (PE) | 0.1 | 0 | 0 | 0.1 | 0.1 | 0 | Controls |
| | IgG2a (PE) | 0.2 | 0 | 0.1 | 0 | 0 | 0 | |
| | IgG1 (FITC) | 0.1 | 0 | 0.1 | 0 | 0 | 0 | |

TABLE 8

| | Marker (dye) | Passage | | | | | | |
|---|---|---|---|---|---|---|---|---|
| | | 0 | 1 | 2 | 3 | 4 | 5 | |
| Sample 5 | CD73 (PE) | 99.9 | 100 | 99.8 | 99.9 | 99.9 | 100 | Positives |
| | CD90 (PE) | 99.9 | 100 | 100 | 99.9 | 99.9 | 100 | |
| | CD105 (PE) | 98.7 | 99.9 | 91.3 | 99.9 | 99.9 | 99.7 | |
| | CD44 (FITC) | 98.8 | 99.9 | 97.4 | 99.8 | 100 | 99.9 | |
| | HLA-DR (PE) | 0.4 | 0.1 | 0.2 | 0.1 | 0.1 | 0.1 | Negatives |
| | CD34 (PE) | 16.7 | 0.2 | 1.1 | 1.4 | 3.7 | 17.6 | |
| | CD45 (PE) | 3.4 | 0 | 0.2 | 1.6 | 0.8 | 0.3 | |
| | CD11b (PE) | 0.4 | 0.1 | 0.6 | 0 | 0 | 0.1 | |
| | CD19 (PE) | 0.3 | 0.1 | 0.1 | 0.2 | 0 | 0.5 | |
| | IgG1 (PE) | 0.3 | 0 | 0 | 0 | 0 | 0 | Controls |
| | IgG2a (PE) | 0.4 | 0 | 0.1 | 0 | 0 | 0.1 | |
| | IgG1 (FITC) | 0.2 | 0 | 0 | 0 | 0 | 0 | |

TABLE 9

| | Marker (dye) | Passage | | | | | | |
|---|---|---|---|---|---|---|---|---|
| | | 0 | 1 | 2 | 3 | 4 | 5 | |
| Sample 6 | CD73 (PE) | No data | 99.3 | 99.9 | 99.9 | 99.9 | 100 | Positives |
| | CD90 (PE) | No data | 100 | 100 | 100 | 99.9 | 100 | |
| | CD105 (PE) | No data | 61.7 | 29.7 | 75.1 | 74.4 | 96.2 | |
| | CD44 (FITC) | No data | 94.5 | 98.4 | 98.9 | 99.7 | 99.8 | |
| | HLA-DR (PE) | No data | 0.1 | 0 | 0.1 | 0.1 | 0.1 | Negatives |
| | CD34 (PE) | No data | 9.5 | 1 | 2.4 | 5.5 | 9.7 | |
| | CD45 (PE) | No data | 1.7 | 0.5 | 0.9 | 0.8 | 2.4 | |
| | CD11b (PE) | No data | 0 | 0.1 | 0 | 0 | 0.7 | |
| | CD19 (PE) | No data | 0.1 | 0 | 0.4 | 0.3 | 2.3 | |
| | IgG1 (PE) | No data | 0.1 | 0 | 0.1 | 0.1 | 0.3 | Controls |
| | IgG2a (PE) | No data | 0.2 | 0.2 | 0.1 | 0.1 | 0.2 | |
| | IgG1 (FITC) | No data | 0 | 0 | 0 | 0 | 0 | |

TABLE 10

|  | Marker (dye) | Passage | | | | | | |
|---|---|---|---|---|---|---|---|---|
|  |  | 0 | 1 | 2 | 3 | 4 | 5 | |
| Sample 7 | CD73 (PE) | 99.9 | 100 | 100 | 99.9 | 100 | 99.9 | Positives |
|  | CD90 (PE) | 99.9 | 100 | 100 | 99.9 | 99.1 | 100 | |
|  | CD105 (PE) | 99.7 | 99.9 | 99.5 | 99.9 | 99.1 | 100 | |
|  | CD44 (FITC) | 99.9 | 100 | 99.8 | 99.7 | 99.8 | 99.9 | |
|  | HLA-DR (PE) | 0.3 | 0.2 | 0.2 | 0.2 | 0.1 | 0.1 | Negatives |
|  | CD34 (PE) | 12 | 0.9 | 10.1 | 0.4 | 3.6 | 0.7 | |
|  | CD45 (PE) | 0.9 | 0.5 | 2.1 | 0.2 | 0.2 | 0.3 | |
|  | CD11b (PE) | 0.1 | 0.1 | 0.6 | 0.1 | 0.1 | 0.1 | |
|  | CD19 (PE) | 0.7 | 0.2 | 0.2 | 0.2 | 0.4 | 0.1 | |
|  | IgG1 (PE) | 0.2 | 0.1 | 0.2 | 0.2 | 0.2 | 0.1 | Controls |
|  | IgG2a (PE) | 0.3 | 0.2 | 0.1 | 0.1 | 0.1 | 0.1 | |
|  | IgG1 (FITC) | 0.2 | 0 | 0.1 | 0 | 0.1 | 0.1 | |

TABLE 11

|  | Marker (dye) | Passage | | | | | | |
|---|---|---|---|---|---|---|---|---|
|  |  | 0 | 1 | 2 | 3 | 4 | 5 | |
| Sample 8 | CD73 (PE) | 99.7 | 100 | 99.7 | 99.8 | 99.7 | 99.9 | Positives |
|  | CD90 (PE) | 99.5 | 99.8 | 99.8 | 99.8 | 99.7 | 99.9 | |
|  | CD105 (PE) | 94 | 99.9 | 99.7 | 92.9 | 95.9 | 89.7 | |
|  | CD44 (FITC) | 99.9 | 100 | 100 | 100 | 100 | 99.9 | |
|  | HLA-DR (PE) | 0.5 | 0.1 | 0.1 | 0.1 | 0.1 | 0.1 | Negatives |
|  | CD34 (PE) | 73 | 0.7 | 0.2 | 0.4 | 0.3 | 4.9 | |
|  | CD45 (PE) | 0.5 | 0.1 | 0.1 | 0.1 | 0.1 | 0.1 | |
|  | CD11b (PE) | 0.3 | 0 | 0 | 0 | 0 | 0 | |
|  | CD19 (PE) | 0.3 | 0 | 0 | 0 | 0 | 0.1 | |
|  | IgG1 (PE) | 0.2 | 0.2 | 0 | 0.2 | 0.1 | 0 | Controls |
|  | IgG2a (PE) | 0.3 | 0.1 | 0 | 0.1 | 0.1 | 0.1 | |
|  | IgG1 (FITC) | 0.2 | 0 | 0 | 0.1 | 0.1 | 0 | |

TABLE 12

|  | Marker (dye) | Passage | | | | | | |
|---|---|---|---|---|---|---|---|---|
|  |  | 0 | 1 | 2 | 3 | 4 | 5 | |
| Sample 9 | CD73 (PE) | 99.9 | 100 | 99.9 | 100 | 99.9 | 100 | Positives |
|  | CD90 (PE) | 99.9 | 99.9 | 99.9 | 99.5 | 99.9 | 100 | |
|  | CD105 (PE) | 99.7 | 100 | 99.7 | 99.7 | 99.9 | 99.8 | |
|  | CD44 (FITC) | 99.8 | 99.8 | 99.8 | 99.9 | 99.8 | 99.9 | |
|  | HLA-DR (PE) | 0.1 | 0 | 0.2 | 0.1 | 0.1 | 0.1 | Negatives |
|  | CD34 (PE) | 4.1 | 2.3 | 0.1 | 3.2 | 1.2 | 2.1 | |
|  | CD45 (PE) | 0.1 | 0.2 | 0 | 0.1 | 0.4 | 0.3 | |
|  | CD11b (PE) | 0.1 | 0 | 0 | 0.1 | 0.1 | 0.1 | |
|  | CD19 (PE) | 0.2 | 0.1 | 0.1 | 0.3 | 0.1 | 0.1 | |
|  | IgG1 (PE) | 0.3 | 0.3 | 0.2 | 0.2 | 0.2 | 0.2 | Controls |
|  | IgG2a (PE) | 0.2 | 0.1 | 0.2 | 0.1 | 0.1 | 0.1 | |
|  | IgG1 (FITC) | 0.1 | 0.1 | 0.1 | 0.1 | 0.1 | 0.2 | |

TABLE 13

|  | Marker (dye) | average | | | | | | |
|---|---|---|---|---|---|---|---|---|
|  |  | Passage | | | | | | |
|  |  | 0 | 1 | 2 | 3 | 4 | 5 | |
| Average | CD73 (PE) | 99.8 | 99.9 | 99.9 | 99.9 | 99.9 | 100.0 | Positives |
|  | CD90 (PE) | 99.4 | 99.9 | 99.9 | 99.9 | 99.8 | 100.0 | |
|  | CD105 (PE) | 94.0 | 90.3 | 90.4 | 94.8 | 94.5 | 96.6 | |
|  | CD44 (FITC) | 99.5 | 99.0 | 99.4 | 99.6 | 99.7 | 99.4 | |

TABLE 13-continued

| | average | | | | | | |
|---|---|---|---|---|---|---|---|
| | | Passage | | | | | |
| Marker (dye) | 0 | 1 | 2 | 3 | 4 | 5 | |
| HLA-DR (PE) | 0.5 | 0.1 | 0.1 | 0.1 | 0.1 | 0.1 | Negatives |
| CD34 (PE) | 19.5 | 2.7 | 2.0 | 4.4 | 3.3 | 6.1 | |
| CD45 (PE) | 1.0 | 2.6 | 0.4 | 1.4 | 0.6 | 0.6 | |
| CD11b (PE) | 0.4 | 0.1 | 0.1 | 0.0 | 0.1 | 0.1 | |
| CD19 (PE) | 0.4 | 0.1 | 0.1 | 0.8 | 0.2 | 0.8 | |
| IgG1 (PE) | 0.2 | 0.1 | 0.1 | 0.1 | 0.1 | 0.1 | Controls |
| IgG2a (PE) | 0.3 | 0.1 | 0.1 | 0.1 | 0.1 | 0.1 | |
| IgG1 (FITC) | 0.3 | 0.0 | 0.0 | 0.0 | 0.0 | 0.0 | |

TABLE 14

| | | StDev | | | | | | |
|---|---|---|---|---|---|---|---|---|
| | | | Passage | | | | | |
| | Marker (dye) | 0 | 1 | 2 | 3 | 4 | 5 | |
| StDev | CD73 (PE) | 0.3 | 0.2 | 0.1 | 0.1 | 0.1 | 0.1 | Positives |
| | CD90 (PE) | 1.1 | 0.1 | 0.1 | 0.2 | 0.3 | 0.0 | |
| | CD105 (PE) | 7.1 | 14.4 | 22.9 | 8.3 | 9.5 | 4.9 | |
| | CD44 (FITC) | 0.4 | 1.8 | 0.9 | 0.3 | 0.2 | 1.3 | |
| | HLA-DR (PE) | 0.4 | 0.1 | 0.1 | 0.1 | 0.1 | 0.1 | Negatives |
| | CD34 (PE) | 22.6 | 3.2 | 3.2 | 7.3 | 2.2 | 5.6 | |
| | CD45 (PE) | 1.1 | 6.7 | 0.7 | 3.1 | 0.7 | 0.7 | |
| | CD11b (PE) | 0.5 | 0.1 | 0.3 | 0.1 | 0.1 | 0.2 | |
| | CD19 (PE) | 0.3 | 0.1 | 0.1 | 1.9 | 0.2 | 1.2 | |
| | IgG1 (PE) | 0.1 | 0.1 | 0.1 | 0.1 | 0.1 | 0.1 | Controls |
| | IgG2a (PE) | 0.1 | 0.1 | 0.1 | 0.1 | 0.1 | 0.1 | |
| | IgG1 (FITC) | 0.3 | 0.0 | 0.1 | 0.1 | 0.1 | 0.1 | |

Example 3—SVF Isolation with Vs. Without Red Blood Cell Lysis

Study Design

Two 150 ml cryopreserved lipoaspirated tissue samples were taken from two different batches stored in vapor phase nitrogen (total of four lipoaspirated tissue samples). The tissue samples were thawed and SVFs were isolated from each sample as will be detailed below. Each tissue sample was processed in the same manner prior to the red blood cell lysis buffer step. At that point, two samples (one from each batch) were subjected to the red blood cell lysis step using ACK lysis buffer (Lonza) (samples designated as "A"), while the other two samples (one from each batch) were not subjected to this step (samples designated as "B"). After the lysis step the SVF isolation process proceeded in the same manner for all samples.

Following SVF isolation cells were counted and the following parameters were measured:
Viable cell number/ml
Dead cell number/ml
Total number of viable cells per sample
Viability percent
Average cell size (um)

Cells from each sample were then seeded and expanded to passage 0 (P0). For each batch, all flasks were harvested when one of the samples reached 70-80% confluency. At P0 the following parameters were measured:
Viable cell number/ml
Dead cell number/ml
Total number of viable cells per sample
Viability percent
Average cell size (μm)
MSC morphology
Immunophenotype (FACS analysis: CD90, CD73, CD45 and CD31)
Time to harvest (days)
Procedure Lipoaspirated Tissue Thawing and SVF Isolation Two 150 ml lipoaspirated tissue samples from two different batches, identified as batch EF137 and batch EF144, were thawed (total of four lipoaspirated tissue samples). Each thawed tissue sample was transferred into a 500 ml centrifuge tube. For each batch, one tube was labeled as "A" and the other as "B". A 150 ml collagenase solution (142 ml PBS, 7.5 ml of 5% collagenase stock solution, 0.6 ml $CaCl_2$ 1 M) was added to each tube and the tubes were incubated at 37° C. in a water bath for approximately half an hour with shaking (130 rpm). Next, 200 ml of DMEM Low Glucose (DMEM LG, Gibco) were added to each tube at room temperature and the tubes were centrifuged for 10 min at 500×g, 21±2° C. At the end of the centrifugation most of the supernatant was removed, leaving approximately 5 ml. The pellet in each tube was resuspended in the remaining supernatant and transferred into a 50 ml conical tube. Next, 45 ml of DMEM LG were added to each 50 ml tube and the tubes were centrifuged for 10 min at 500×g, 21±2° C. Following this second centrifugation the supernatant was removed and the pellet in the tubes designated as "B" was resuspended in 5 ml of DMEM LG.

For tubes designated as "A", the pellet was resuspended in 10 ml of ACK red blood cell lysis buffer and incubated for approximately 10 min at 15-25° C. Next, 20 ml of PBS (15-25° C.) were added to the tube and the tube was centrifuged for 10 min at 500×g, 21±2° C. Following centrifugation, the supernatant was removed and the pellet was resuspended in 5 ml of DMEM LG.

Both tubes designated A and tubes designated B were then subjected to two filtration steps in a similar manner: a 100 μm mesh filter was placed on top of new pre-labeled 50 ml tubes (labeled as "A" or "B") and the suspensions were filtered. Each filter was washed with additional 5 ml DMEM LG and the filtrate was then centrifuged for 10 min at 500×g, 21±2° C. The pellets were resuspended in 5 ml DMEM LG. Next, a 40 μm filter was placed on top of another set of new pre-labeled 50 ml tubes (labeled as "A" or "B") and the suspensions were filtered. Each filter was washed with additional 5 ml DMEM LG and the filtrate was then centrifuged for 10 min at 500×g, 21±2° C. Each pellet was resuspended in 5 ml StemMACS™ Complete growth medium (Miltenyi).

SVF Cell Counting and SVF Seeding

NC-200 Nucleo-Counter was used to count the number of cells in each tube. The following parameters were recorded:

viable cells/ml, dead cells/ml, viability (%), average cell size (μm) and total number of viable cells. Each tube was counted twice and an average of the two counts was calculated.

Next, $2.6 \times 10^6$ cells from each tube were seeded in 75 cm² flasks in duplicates and 15 ml of StemMACS™ Complete growth medium were added to each flask. The flasks were incubated overnight to select for plastic adherent cells (ADSCs). The next day the flasks were washed to remove non-adherent cells and tissue debris, fresh medium was added and cells were allowed to grow. Cells were harvested when one of the groups reached approximately 80% confluence.

Harvesting of P0

Cells were harvested and counted. The following parameters were recorded: viable cells/ml, dead cells/ml, viability (%), average cell size (μm), total number of viable cells, and time from seeding to harvest (days). Each tube was counted twice and an average of the two counts was calculated.

Immunophenotype—P0

Cells from each tube were analyzed by FACS for the following markers: CD73, CD90, CD45, CD31, and IgG1 as a control.

Results

Tables 15 and 17 below and FIGS. 8A-8B, 9A-9B show cell counting data (average of two counts for each sample) immediately after SVF isolation and at passage 0 (P0). The standard deviation (SD) data are summarized in Tables 16, 18.

TABLE 15

Cell count following SVF isolation

| | Batch | | | |
|---|---|---|---|---|
| | EF137 | | EF144 | |
| | Sample | | | |
| | A | B | A | B |
| Viable cells/ml | 8.56E+06 | 8.51E+06 | 2.59E+06 | 5.63E+06 |
| Dead cells/ml | 2.72E+06 | 2.93E+06 | 5.64E+05 | 1.33E+06 |
| Viability % | 75.9 | 74.4 | 82.3 | 80.9 |
| Av. cell size (micrometer) | 9.85 | 9.7 | 10.4 | 10.15 |
| Total number of viable cells | 4.28E+07 | 4.25E+07 | 1.30E+07 | 2.82E+07 |

TABLE 16

SD of cell count following SVF isolation

| | Batch | | | |
|---|---|---|---|---|
| | EF137 | | EF144 | |
| | Sample | | | |
| | A | B | A | B |
| Viable cells/ml | 2.47E+05 | 1.63E+05 | 2.55E+05 | 7.07E+04 |
| Dead cells/ml | 6.36E+04 | 1.20E+05 | 1.47E+05 | 1.77E+05 |
| Viability % | 0.14 | 1.13 | 2.40 | 1.84 |
| Av. cell size (micrometer) | 0.070711 | 0 | 0 | 0.070711 |
| Total number of viable cells | 1.24E+06 | 8.13E+05 | 1.27E+06 | 3.54E+05 |

TABLE 17

Cell count at P0

| | Batch | | | |
|---|---|---|---|---|
| | EF137 | | EF144 | |
| | Sample | | | |
| | A | B | A | B |
| Viable cells/ml | 4.81E+05 | 9.04E+05 | 1.30E+06 | 2.07E+06 |
| Dead cells/ml | 1.32E+04 | 3.08E+04 | 7.79E+04 | 1.42E+05 |
| Viability % | 97.325 | 96.7 | 94.325 | 93.475 |
| Av. cell size (micrometer) | 13.75 | 13.425 | 13.475 | 13.425 |
| Total number of viable cells | 2.41E+06 | 4.52E+06 | 6.50E+06 | 1.03E+07 |

TABLE 18

SD of cell count at P0

| | Batch | | | |
|---|---|---|---|---|
| | EF137 | | EF144 | |
| | Sample | | | |
| | A | B | A | B |
| Viable cells/ml | 2.08E+04 | 1.18E+05 | 8.60E+04 | 3.23E+05 |
| Dead cells/ml | 8.49E+03 | 7.16E+03 | 5.09E+04 | 4.55E+04 |
| Viability % | 1.763283 | 0.374166 | 3.757104 | 2.478407 |
| Av. cell size (micrometer) | 0.208167 | 0.095743 | 0.170783 | 0.15 |
| Total number of viable cells | 1.04E+05 | 5.90E+05 | 4.30E+05 | 1.61E+06 |

As can be seen from the tables and figures, cell counting data were essentially the same, and for some parameters even better, for samples that were not subjected to the red blood cell lysis (samples designated as "B") and those subjected to the lysis step (samples designated as "A"), indicating that omission of the lysis step does not negatively affect the growth of the cells.

Advantageously, at P0, samples that were not subjected to the red blood cell lysis reached 70-80% confluency faster than samples that were subjected to the lysis step.

Table 19 summarizes the immunophenotype data (marker expression) at passage 0.

As can be seen from the table, marker expression was essentially the same for samples not subjected to the red blood cell lysis and for samples that were subjected to the lysis step, indicating that omission of this step does not negatively affect the phenotype of the obtained cells.

TABLE 19

Marker expression (%) at P0

| | Batch | | | |
|---|---|---|---|---|
| | EF137 | | EF144 | |
| | Sample | | | |
| | A | B | A | B |
| CD73 | 99.9 | 99.85 | 99.9 | 99.9 |
| CD90 | 99.65 | 99.9 | 99.95 | 99.85 |
| CD45 | 0.25 | 0.3 | 0.3 | 0.25 |
| CD31 | 5.85 | 1.9 | 3.75 | 4.15 |

To conclude, it was found that even though a red blood cell lysis buffer is not applied, the resulting ADSC sample grows as effectively as a sample isolated according to standard methods employing red blood cell lysis.

Example 4—Effect of Initial Tissue Volume on the Yield of Stromal Vascular Fraction (SVF) and Adipose-Derived Stem Cells (ADSCs)

The amount of ADSCs that can be obtained from a lipoaspirated tissue sample depends, among others, on the initial volume of the lipoaspirated tissue sample. For therapeutic applications such as treating multiple sclerosis as described herein, it is suggested that at least $10^5$ ADSCs be obtained, or even at least $10^6$ ADSCs.

The following study aimed at defining a minimum volume of fat tissue (lipoaspirated tissue) that can be used in order to obtain an amount of ADSCs that is sufficient for therapeutic purposes such as treating multiple sclerosis according to the present invention, and at evaluating possible changes to the production process that may improve the yield in cases where volumes lower than 100 ml are available for processing.

Study Design

Three different batches of human lipoaspirated tissue were obtained. From each batch, samples of 5, 10, 20, 50 and 150 ml were washed with PBS and placed in freezing bags. DMSO was added at a final concentration of 10% and the samples were stored in liquid nitrogen until use.

SVF Production

All samples were thawed and processed to obtain SVF without applying red blood cell lysis, as described in Examples 1 and 3 above. The samples of 5, 10, 20 and 50 ml were processed without applying filtration (i.e., the steps of filtering through a 100 μm filter and subsequently through a 40 μm filter were omitted, in addition to the omission of the red blood cell lysis).

Cell Culture

The SVF fractions obtained from the 20, 50 and 150 ml samples were seeded at a concentration of $35 \times 10^3$/cm$^2$. The SVF fractions obtained from the 5 and 10 ml samples were seeded at a concentration of $\sim 4 \times 10^3$ cells/cm$^2$. Following overnight incubation to select for plastic adherent cells (ADSCs), the flasks were washed, fresh medium was added, and the cells were grown in StemMACS™ Complete medium to ~80% confluency. At this stage the cell passage was defined as P #0. Cells were then trypsinized, harvested, seeded in fresh flasks at a concentration of $5 \times 10^3$ cells/cm$^2$, and grown again to ~80% confluency to the next passage, defined as P #1. Cells were then trypsinized, harvested, and kept frozen at a concentration of $\sim 5 \times 10^6$/ml in 1 ml cryotubes until use.

In addition, during the processing of the 50 ml samples, a large number of tissue aggregates were observed following tissue digestion and centrifugation, and it was decided to examine if the aggregates can also yield mesenchymal stem cells when processed separately. The aggregates were collected and seeded in separate flasks and incubated overnight to select for plastic-adherent cells. The non-adherent cells were washed and the remaining sample was further processed in the same manner as the other samples.

Analysis:

Cells were thawed and the number of cells, cell viability and cell diameter were determined immediately after thawing. For FACS analysis cells were allowed to recover overnight (1 frozen vial seeded in a 175 cm$^2$ flask) prior to the analysis.

Results

Tables 20-22 below and FIGS. 10A-C, 11A-C, 12A-C show cell counting data for each sample immediately after SVF isolation and at passages 0 and 1 (P #0, P #1).

TABLE 20

1$^{st}$ batch
Total number of viable cells (×10$^6$)

|  | 5 ml | 10 ml | 20 ml | 50 ml | 50 ml Aggregates | 150 ml |
|---|---|---|---|---|---|---|
| SVF | 3.34 | 1.97 | 3.27 | 3.27 | NA | 11.00 |
| P#0 | 1.81 | 0.49 | 9.51 | 0.75 | 6.00 | 11.50 |
| P#1 | 36.80 | 5.90 | 152.68 | 12.54 | 114.73 | 124.80 |

TABLE 21

2$^{nd}$ batch
Total number of viable cells (×10$^6$)

|  | 5 ml | 10 ml | 20 ml | 50 ml | 50 ml Aggregates | 150 ml |
|---|---|---|---|---|---|---|
| SVF | 0.99 | 2.53 | 2.71 | 6.70 | NA | 30.28 |
| P#0 | 0.89 | 2.43 | 1.97 | 9.77 | 10.90 | 19.70 |
| P#1 | 13.06 | 30.50 | 21.50 | 100.25 | 156.56 | 98.00 |

TABLE 22

3$^{rd}$ batch
Total number of viable cells (×10$^6$)

|  | 5 ml | 10 ml | 20 ml | 50 ml | 50 ml Aggregated | 150 ml |
|---|---|---|---|---|---|---|
| SVF | 0.61 | 0.53 | 7.13 | 9.03 | NA | 8.70 |
| P#0 | 0.82 | 0.72 | 7.65 | 10.30 | 4.10 | 9.30 |
| P#1 | 4.43 | 4.78 | 102.40 | 99.00 | 72.78 | 68.60 |

Large variability was seen in the SVF yield between the three different batches. In addition, the number of cells in the SVF fraction did not always correlate with the number of cells obtained at P #0. However, once a selected MSC population was harvested (P #0), the further expansion to P #1 correlated with the number of MSC cells at P #0, and at P #1 the number of cells of a given batch correlated with the number of cells of this batch at P #0.

As described above, the 50 ml samples were not filtered and large aggregates were observed. The aggregates were collected and seeded separately (rather than discarded, as normally done). The aggregates produced a large number of MSCs, and therefore it was concluded that it is advantageous to keep and culture aggregates for yield increase.

FACS Analysis:

The P #1 samples of the three batches were harvested and cryopreserved at a concentration of $\sim 5 \times 10^6$ cells/ml. The cells were then thawed, seeded overnight with StemMACS™ Complete, harvested and analyzed by FACS. The markers that were analyzed are listed in Table 23. The results of the analysis are specified in Tables 24-27.

TABLE 23 markers for FACS analysis

| Markers | |
|---|---|
| CD73-PE | Positive |
| CD90-PE | |
| CD105-PE | |
| CD44-FITC | |
| HLA-DR-PE | Negative |
| CD34-PE | |
| CD45-PE | |
| CD11b-PE | |
| CD19-PE | |
| IgG1-PE | Control |
| IgG2a-PE | |
| IgG1-FITC | |

TABLE 24

FACS analysis - positive markers

| Volume | Batch | CD73-PE | CD90-PE | CD105-PE | CD44-FITC |
|---|---|---|---|---|---|
| 5 ml | 1st | 99.9 | 99.9 | 96.9 | 99.7 |
|  | 2nd | 99.8 | 99.8 | 95.0 | 98.8 |
|  | 3rd | 99.9 | 99.9 | 99.8 | 99.8 |
|  | Average | 99.9 | 99.9 | 97.2 | 99.4 |
| 10 ml | 1st | 99.9 | 99.6 | 98.5 | 98.7 |
|  | 2nd | 99.9 | 99.8 | 99.4 | 99.5 |
|  | 3rd | 99.9 | 99.9 | 99.8 | 99.6 |
|  | Average | 99.9 | 99.8 | 99.2 | 99.3 |
| 20 ml | 1st | 99.9 | 99.9 | 98.5 | 99.3 |
|  | 2nd | 99.6 | 99.5 | 98.4 | 98.5 |
|  | 3rd | 99.9 | 99.9 | 99.8 | 99.7 |
|  | Average | 99.8 | 99.8 | 98.9 | 99.2 |
| 50 ml | 1st | 99.9 | 99.9 | 99.4 | 99.2 |
|  | 2nd | 99.9 | 99.9 | 99.9 | 99.0 |
|  | 3rd | 99.7 | 99.8 | 99.4 | 99.5 |
|  | Average | 99.8 | 99.9 | 99.6 | 99.2 |
| 50 ml Aggregated | 1st | 99.9 | 99.9 | 99.5 | 99.1 |
|  | 2nd | 100.0 | 99.9 | 99.9 | 99.7 |
|  | 3rd | 99.8 | 99.6 | 95.9 | 98.9 |
|  | Average | 99.9 | 99.8 | 98.4 | 99.2 |
| 150 ml | 1st | 99.9 | 99.9 | 99.9 | 99.7 |
|  | 2nd | 100.0 | 99.9 | 99.9 | 99.9 |
|  | 3rd | 99.9 | 99.8 | 99.5 | 99.9 |
|  | Average | 99.9 | 99.9 | 99.8 | 99.8 |

TABLE 25

Positive markers - average and SD

| | CD73-PE | CD90-PE | CD105-PE | CD44-FITC |
|---|---|---|---|---|
| Average | | | | |
| 5 ml | 99.9 | 99.9 | 97.2 | 99.4 |
| 10 ml | 99.9 | 99.8 | 99.2 | 99.3 |
| 20 ml | 99.8 | 99.8 | 98.9 | 99.2 |
| 50 ml | 99.8 | 99.9 | 99.6 | 99.2 |
| 50 ml Aggregated | 99.9 | 99.8 | 98.4 | 99.2 |
| 150 ml | 99.9 | 99.9 | 99.8 | 99.8 |
| SD (n = 3) | | | | |
| 5 ml | 0.1 | 0.1 | 2.4 | 0.6 |
| 10 ml | 0.0 | 0.2 | 0.7 | 0.5 |
| 20 ml | 0.2 | 0.2 | 0.8 | 0.6 |
| 50 ml | 0.1 | 0.1 | 0.3 | 0.3 |
| 50 ml Aggregated | 0.1 | 0.2 | 2.2 | 0.4 |
| 150 ml | 0.1 | 0.1 | 0.2 | 0.1 |

TABLE 26

FACS analysis - negative markers

| Volume | Batch | HLA-DR-PE | CD34-PE | CD45-PE | CD11b-PE | CD19-PE |
|---|---|---|---|---|---|---|
| 5 ml | 1st | 0.0 | 0.2 | 0.1 | 0.0 | 0.1 |
|  | 2nd | 0.2 | 7.1 | 2.4 | 0.4 | 0.8 |
|  | 3rd | 0.3 | 0.3 | 0.1 | 0.0 | 0.1 |
|  | Average | 0.2 | 2.5 | 0.9 | 0.1 | 0.3 |
| 10 ml | 1st | 0.2 | 0.6 | 0.2 | 0.1 | 0.1 |
|  | 2nd | 0.1 | 35.6 | 6.5 | 1.0 | 4.8 |
|  | 3rd | 0.3 | 9.3 | 6.9 | 0.1 | 8.6 |
|  | Average | 0.2 | 15.2 | 4.5 | 0.4 | 4.5 |
| 20 ml | 1st | 0.2 | 0.6 | 0.2 | 0.1 | 0.0 |
|  | 2nd | 0.3 | 68.8 | 5.0 | 0.4 | 1.3 |
|  | 3rd | 0.1 | 2.1 | 0.8 | 0.2 | 1.3 |
|  | Average | 0.2 | 23.8 | 2.0 | 0.2 | 0.9 |
| 50 ml | 1st | 0.1 | 19.7 | 0.8 | 0.2 | 1.8 |
|  | 2nd | 0.2 | 41.7 | 12.8 | 0.2 | 12.4 |
|  | 3rd | 0.1 | 9.4 | 0.3 | 0.2 | 0.9 |
|  | Average | 0.1 | 23.6 | 4.6 | 0.2 | 5.0 |
| 50 ml Aggregated | 1st | 0.2 | 28.4 | 7.0 | 0.2 | 9.4 |
|  | 2nd | 0.2 | 78.4 | 33.6 | 2.1 | 12.9 |
|  | 3rd | 0.1 | 18.8 | 0.8 | 0.6 | 0.1 |
|  | Average | 0.2 | 41.9 | 13.8 | 1.0 | 7.5 |
| 150 ml | 1st | 0.0 | 7.0 | 4.2 | 0.0 | 0.6 |
|  | 2nd | 0.1 | 23.2 | 4.9 | 0.1 | 4.2 |
|  | 3rd | 0.2 | 4.6 | 1.1 | 0.5 | 0.3 |
|  | Average | 0.1 | 11.6 | 3.4 | 0.2 | 1.7 |

TABLE 27 negative markers - average and SD

| | HLA-DR-PE | CD34-PE | CD45-PE | CD11b-PE | CD19-PE |
|---|---|---|---|---|---|
| Average | | | | | |
| 5 ml | 0.2 | 2.5 | 0.9 | 0.1 | 0.3 |
| 10 ml | 0.2 | 15.2 | 4.5 | 0.4 | 4.5 |
| 20 ml | 0.2 | 23.8 | 2.0 | 0.2 | 0.9 |
| 50 ml | 0.1 | 23.6 | 4.6 | 0.2 | 5.0 |
| 50 ml Aggregated | 0.2 | 41.9 | 13.8 | 1.0 | 7.5 |
| 150 ml | 0.1 | 11.6 | 3.4 | 0.2 | 1.7 |
| SD (n = 3) | | | | | |
| 5 ml | 0.2 | 4.0 | 1.3 | 0.2 | 0.4 |
| 10 ml | 0.1 | 18.2 | 3.8 | 0.5 | 4.3 |
| 20 ml | 0.1 | 38.9 | 2.6 | 0.2 | 0.8 |
| 50 ml | 0.1 | 16.5 | 7.1 | 0.0 | 6.4 |
| 50 ml Aggregated | 0.1 | 32.0 | 17.4 | 1.0 | 6.6 |
| 150 ml | 0.1 | 10.1 | 2.0 | 0.3 | 2.2 |

The positive markers showed a high percentage of mesenchymal stem cells (as defined by the ISCT guidelines) in all of the processed volumes from all of the three tested batches (Positive CD73, CD105, CD90, CD44).

The negative markers showed higher percentages than what is normally seen for adipose-derived mesenchymal stem cells, indicating the presence of hematopoietic progenitors as impurities. In a separate series of experiments cells were cultured for five (5) passages, and it was demonstrated that the negative markers are decreased as a function of passage.

In non-filtered samples tissue aggregates may trap more hematopoietic progenitors, which result in higher expression of CD34 as well as higher CD45 and CD19 expressing cells. This assumption is supported by 50 ml-aggregates cultures, which displayed the highest CD34 expression.

To conclude, despite the large variability, the results show that sufficient amounts of ADSCs for therapeutic applications such as treatment of MS as disclosed herein can be obtained even from very low initial tissue volumes. To utilize the low initial volumes, certain adaptations to the production process may be applied, such as omission of filtration and culturing for at least 4 passages, in order to reduce loss of cells and obtain an ADSC population with sufficient purity.

If possible, it is suggested to use initial tissue volumes of at least 50 ml. It is further suggested to apply a production process which includes filtration through a set of filters (but is devoid of red blood cell lysis, as disclosed herein), inter alia, to improve the purity of the ADSCs at earlier passages.

However, if the volume of a lipoaspirated tissue collected from a patient is less than 50 ml, and it is not possible to collect more, the adapted process may be applied.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A method of treating primary progressive multiple sclerosis comprising administering non-genetically modified human adipose-derived stem cells (hADSCs) into the central nervous system (CNS) of a subject in need thereof, wherein the hADSCs are:
    (a) isolated hADSCs obtained by processing a stromal vascular fraction (SVF) derived from an adipose tissue to separate the hADSCs;
    (b) sub-cultured to a passage number between 3-10 passages; and
    (c) characterized by positive expression of CD34 by 1-10% of the cells.

2. The method of claim 1, wherein the hADSCs are hADSCs obtained from human subcutaneous fat by:
    (a) freezing a lipoaspirate;
    (b) thawing the lipoaspirate and dissociating with a tissue-dissociation enzyme or by mechanical disruption;
    (c) pelleting a cellular fraction comprising the hADSCs by centrifugation and optionally washing the pellet with a suspension medium capable of supporting cell viability and subjecting the suspension to at least one additional centrifugation;
    (d) resuspending the pellet obtained in step (c) in a suspension medium capable of supporting cell viability and selecting hADSCs from the population of cells in the resuspended pellet;
    (e) optionally conducting at least one filtration prior to the hADSC selection; and
    (f) optionally culturing the hADSCs for at least 3 passages.

3. The method of claim 2, wherein the cellular fraction comprising the hADSCs obtained following centrifugation is not exposed to a red blood cell lysis buffer.

4. The method of claim 2, wherein the hADSCs are selected by adherence to the cell culture vessel.

5. The method of claim 2, wherein said freezing is carried out at −80° C. followed by vapor phase liquid nitrogen.

6. The method of claim 2, wherein the tissue-dissociation enzyme is selected from a collagenase, a dispase or a combination thereof.

7. The method of claim 2, wherein the hADSCs are characterized by positive expression of CD44, CD73 and CD90 by at least 95% of the cells, positive expression of CD105 by at least 90% of the cells, and negative expression of CD45, CD19, CD11b and HLA-DR by at least 95% of the cells.

8. The method of claim 2, wherein at least 50% of the cells are positive for CD105, CD73, CD44 and CD90, and negative for CD45, CD19, CD11b and HLA-DR.

9. The method of claim 1, wherein administering the hADSCs is by intrathecal, intraventricular or intracerebroventricular (ICV) administration.

10. The method of claim 1, wherein administering the hADSCs comprises administrating about $10^5$–$3\times10^8$ cells per one administration.

* * * * *